(12) United States Patent
Mobashery et al.

(10) Patent No.: US 6,703,415 B2
(45) Date of Patent: Mar. 9, 2004

(54) INHIBITORS OF MATRIX METALLAPROTEINASES

(75) Inventors: Shahriar Mobashery, Portage, MI (US); Rafael Fridman, West Bloomfield, MI (US)

(73) Assignee: Wayne State University, Detroit, MI (US)

( * ) Notice: Subject to any disclaimer, the term of this patent is extended or adjusted under 35 U.S.C. 154(b) by 17 days.

(21) Appl. No.: 09/870,403

(22) Filed: May 3, 2001

(65) Prior Publication Data

US 2002/0037916 A1 Mar. 28, 2002

Related U.S. Application Data

(60) Provisional application No. 60/226,858, filed on Aug. 22, 2000, and provisional application No. 60/207,874, filed on May 30, 2000.

(51) Int. Cl.$^7$ ...................... A61K 31/38; A61K 31/335; C07D 327/02; C07D 303/00; C07D 303/12
(52) U.S. Cl. ...................... 514/430; 514/475; 549/90; 549/512; 549/555; 549/554; 549/556
(58) Field of Search ................................ 514/430, 475; 549/90, 554, 555, 556, 512

(56) References Cited

U.S. PATENT DOCUMENTS

| | | | | |
|---|---|---|---|---|
| 2,949,474 A | * | 8/1960 | Murdoch et al. | 514/430 |
| 2,965,651 A | * | 12/1960 | Kosmin | 514/430 |
| 3,222,326 A | * | 12/1965 | Brodoway | 514/430 |
| 4,797,218 A | * | 1/1989 | Steinberg et al. | 549/90 |
| 5,288,722 A | * | 2/1994 | Kishimoto et al. | 514/475 |
| 5,981,763 A | * | 11/1999 | Garapon et al. | 549/512 |

FOREIGN PATENT DOCUMENTS

| WO | WO-95/35275 | 12/1995 |
|---|---|---|
| WO | WO-97/18231 | 5/1997 |
| WO | WO-98/33788 | 8/1998 |

OTHER PUBLICATIONS

Beckett, R.P., et al., "Recent Advances in Matrix Metalloproteinase Inhibitor Research", *Drug Disc. Today, 1*, (1996), pp. 16–26.

Brew, K., et al., "Tissue Inhibitors of Metalloproteinases: Evolution, Structure and Function", *Biochim. Biophys. Acta, 1477*, (2000), pp. 267–283.

Brown, S., et al., "Potent and Selective Mechanism–Based Inhibition of Gelatinases", *J. Am. Chem. Soc., 122*, (2000), pp. 6799–6800.

Bulychev, A., et al., "N–Sulfonyloxy–β–lactam Inhibitors for β–Lactamases", *Tetrahedron, 56*, (2000), pp. 5719–5728.

Dalberg, K.,et al., "Gelatinase A, Membrane Type 1 Matrix Metalloproteinase, and Extracellular Matrix Metalloproteinase Inducer mRNA Expression: Correlation with Invasive Growth of Breast Cancer", *World J. Surg., 24*, (2000), pp. 334–340.

Dumas, V., et al., "Expression of Basement Membrane Antigens and Matrix Metalloproteinases 2 and 9 in Cutaneous Basal and Squamous Cell Carcinomas", *A. Anticancer Res., 19*, (1999), pp. 2929–2938.

Forget, A–M, et al., "Physiological Roles of Matrix Metalloproteinases: Implications for Tumor Growth and Metastasis", *Can. J. Physiol. Pharmacol, 77*, (1999), pp. 465–480.

Freskos, J., "Discovery of a Novel Series of Selective MMP Inhibitors: Identification of the γ–Sulfone–Thiols", *Bioorg. & Med. Chem. Letters, 9*, (1999), pp. 943–948.

Fridman, R., et al., "Domain Structure of Human 72–kDa Gelatinase/Type IV Collagenase", *J. Biol. Chem., 267*, (1992), pp. 15398–15405.

Fridman, R., et al., "Expression of Human Recombinant 72 kDa Gelatinase and Tissue Inhibitor of Metallorproteinase–2 (TIMP–2): Characterization of Complex and Free Enzyme", *Biochem. J., 289*, (1993), pp. 411–416.

Greenwald, R.A., et al., "Inhibition of Matrix Metalloproteinase Therapeutic Applications", *Ann. N. Y. Acad. Sci., 878*, (1999), pp. 412–419.

Knight, C.G., "Fluorimetric Assays of Proteolytic Enzymes", *Methods Enzymol., 248*, (1995), pp. 18–34.

Massova, I., et al., "Matrix Metalloproteinases: Structures, Evolution, and Diversification", *FASEB J., 12*, (1998), pp. 1075–1095.

Massova, I., et al., "Structural Insights into the Catalytic Domains of Human Matrix Metalloprotease–2 and Human Matrix Metalloprotease–9: Implications for Substrate Specifities", *FASEB J., 12*, (1998), pp. 17–30.

Michaelides, M.R., et al., "Recent Advances In Matrix Metalloproteinase Inhibitors Research", *Curr. Pharm. Des. 5*, (1999), pp. 787–819.

Morgunova, E., et al., "Structure of Human Pro–Matrix Metalloproteinase–2: Activation Mechanism Revealed", *Science, 284*, (1999), pp. 1667–1670.

Nelson, A.R., et al., "Matrix Metalloproteinases: Biologic Activity and Clinical Implications", *J. Clin. Oncol, 18*, (2000), pp. 1135–1149.

(List continued on next page.)

*Primary Examiner*—Deborah C. Lambkin
(74) *Attorney, Agent, or Firm*—Schwegman, Lundberg, Woessner & Kluth, P.A.

(57) ABSTRACT

The invention provides compounds that inhibit MMPs; methods for treating or preventing cancer, angiogenesis, arthritis, connective tissue disease, cardiovascular disease, inflammation or autoimmune disease in a mammal; a method for inhibiting a matrix metalloproteinase in vivo or in vitro; and a method for imaging a tumor in vivo or in vitro.

30 Claims, 3 Drawing Sheets

OTHER PUBLICATIONS

Olson, M., et al., "Characterization of the Monomeric and Dimeric Forms of Latent and Active Matrix Metalloproteinase-9", *J. Biol. Chem., 275*, (2000), pp. 2661–2668.

Pyke, C., et al., "Localization of Messenger RNA for $M_r$ 72,000 and 92,000 Type IV Collagenases in Human Skin Cancers by in Situ Hybridization", *Cancer Res., 52*, (1992), pp. 1336–1341.

Salo, T., et al., "Purification and Characterization of a Murine Basement Membrane Collagen–degrading Enzyme Secreted by Metastatic Tumor Cells", *J. Biol. Chem., 258*, pp. 3058–3063.

Tamura, Y., "Highly Selective and Orally Active Inhibitors of Type IV Collagenase (MMP–9 and MMP–2): N–Sulfonylamino Acid Derivatives", *J. Med. Chem., 41*, (1998), pp. 640–649.

Westermarck, J., et al., "Regulation of Matrix Metalloproteinase Expression in Tumor Invasion", *FASEB J., 13*, (1999), pp. 781–792.

\* cited by examiner

INHIBITORS OF MATRIX METALLAPROTEINASES

RELATED APPLICATION

The present application claims priority under 35 U.S.C. 119 to U.S. Provisional Application Ser. No. 60/207,874; filed May 30, 2000 and U.S. Provisional Application Ser. No. 60/226,858; filed August 22, 2000; which applications are incorporated herein by reference.

BACKGROUND OF THE INVENTION

Specific interactions of cells within the extracellular matrix are critical for the normal function of organisms. Alterations of the extracellular matrix are carried out by a family of zinc-dependent endopeptidases called matrix metalloproteinases (MMPs). The alterations are carried out in various cellular processes such as organ development, ovulation, fetus implantation in the uterus, embyiogenesis, wound healing, and angiogenesis. Massova, I.; Kotra, L. P.; Fridman, R.; Mobashery, S. *FASEB J* 1998, 12, 1075; Forget, M. -A.; Desrosier, R. R.; Béliveau, R. *Can. J Physiol. Pharmacol.* 1999, 77, 465–480.

MMPs consist of five major groups of enzymes: gelatinases, collagenases, stromelysins, membrane-type MMPs, and matrilysins. The activities of MMPs in normal tissue functions is strictly regulated by a series of complicated zymogen activation processes and inhibition by protein tissue inhibitors for matrix metalloproteinases ("TIMPs"). Forget, M. -A.; Desrosier, R. R.; Béliveau, R. *Can. J. Physiol. Pharmacol.* 1999, 77, 465–480; Brew, K.; Dinakarpandian, D.; Nagase, H. *Biochim. Biophys. Acta* 2000, 1477, 267–283. Westermarck, J.; Kahari, V. M. *FASEB J.* 1999, 13, 781–792. Excessive MMP activity, when the regulation process fails, has been implicated in cancer growth, tumor metastasis, angiogenesis in tumors, arthritis and connective tissue diseases, cardiovascular disease, inflammation and autoimmune diseases. Massova, I.; Kotra, L. P.; Fridman, R.; Mobashery, S. *FASEB J.* 1998, 12, 1075; Forget, M. -A.; Desrosier, R. R.; Béliveau, R. *Can. J Physiol. Pharmocol.* 1999, 77, 465–480; Nelson, A. R.; Fingleton, B.; Rothenberg, M. L.; Matrisian, L. M. *J. Clin. Oncol.* 2000, 18, 1135.

Increased levels of activity for the human gelatinases MMP-2 and MMP-9 have been implicated in the process of tumor metastasis. Dalberg, K.; Eriksson, E.; Enberg, U.; Kjellman, M.; Backdahl, M. *World J. Surg.* 2000, 24, 334–340. Salo, T.; Liotta, L. A.; Tryggvason, K. *J BioL Chem.* 1983, 258, 3058–3063. Pyke, C.; Ralfkiaer, E.; Huhtala, P.; Hurskainen, T.; Dano, K.; Tryggvason, K. *Cancer Res.* 1992, 52, 1336–1341. Dumas, V.; Kanitakis, J.; Charvat, S.; Euvrard, S.; Faure, M.; Claudy, A. *Anticancer Res.* 1999, 19, 2929–2938. As a result, select inhibitors of MMPs (e.g., MMP-2 and MMP-9) are highly sought.

Several competitive inhibitors of MMPs are currently known. These inhibitors of MMPs take advantage of chelation to the active site zinc for inhibition of activity. Because of this general property, these competitive inhibitors for MMPs are often toxic to the host, which has been a major impediment in their clinical use. Greenwald, R. A. *Ann. N. Y Acad. Sci.* 1999, 878, 413–419; (a) Michaelides, M. R.; Curtin, M. L. *Curr. Pharm. Des.* 1999, 5, 787–819. (b) Beckett, R. P.; Davidson, A. H.; Drummond, A. H.; Huxley, P.; Whittaker, M. *Drug Disc. Today* 1996, 1, 16–26.

Gelatinases have been shown to function in both female ovulation and inplantation of zygotes in the womb. The female contains a pair of gonads, a system of ducts and chambers to conduct the gametes as well as to house the embryo and fetus, and external genitalia that facilitate reproductive function. The female gonads, the ovaries, lie in the abdominal cavity below most of the digestive system. Each ovary is enclosed in a tough protective capsule and contains many follicles. A follicle consists of one egg cell surrounded by one or more layers of follicle cells, which nourish and protect the developing egg cell. All of the 400,000 follicles a woman will ever have are formed at birth. Of these, only several hundred will be released during the woman's reproductive years. After puberty, one (or rarely two or more) follicle matures and releases its egg during each menstrual cycle. The cells of the follicle also produce the primary female sex hormones, the estrogen. When ovulation occurs, the egg is expelled from the follicle (much like a small volcano), and the remaining follicular tissue grows within the ovary to form a solid mass called the corpus luteum. The corpus luteum secretes progesterone, the hormone of pregnancy, and additional estrogen. If the egg is not fertilized, the corpus luteum degenerates and a new follicle matures during the next cycle.

The female reproductive system is not completely closed, and the egg cell is expelled into the abdominal cavity near the opening of the oviduct, or fallopian tube. The oviduct has a funnellike opening, and cilia on the inner epithelium lining the duct help collect the egg cell by drawing fluid from the body cavity into the duct. The cilia also convey the egg cell down the duct to the uterus, commonly called the womb. The uterus is a thick, muscular organ shaped much like an upside-down pear. It is remarkably small; the uterus of a woman who has never been pregnant is about 7 cm long and 4–5 cm wide at its widest point. The unique arrangement of muscles that make up the bulk of the uterine wall allow it to expand to accommodate a 4-kg fetus. The inner lining of the uterus, the endometrium, is richly supplied with blood vessels.

The pattern of hormone secretion controlling female reproduction differs strikingly from the male pattern, reflecting a cyclic nature of female reproduction.

Two different types of cycles occur in female mammals. Humans and many other primates have menstrual cycles, whereas other mammals have estrous cycles. In both cases, ovulation occurs at a time in the cycle after the endometrium has started to thicken and become more extensively vascularized, which prepares the uterus for the possible implantation of an embryo.

The menstrual cycle averages 28 days, but only about 30% of women have cycle lengths within a day or two of the statistical 28 days. Cycles vary from one woman to another, ranging from about 20 to 40 days. In some women the cycles are usually very regular, but in other individuals the timing varies from cycle to cycle.

Paralleling the menstrual cycle is an ovarian cycle. It begins with the follicular phase, during which several follicles in the ovary begin to grow. The egg cell enlarges and the coat of follicle cells becomes multi-layered. Of the several follicles that start to grow, only one usually continues to enlarge and mature, while the others degenerate. The maturing follicle develops an internal fluid-filled cavity and grows very large, forming a bulge near the surface of the ovary. The follicular phase ends with ovulation when the follicle and adjacent wall of the ovary rupture, releasing the egg cell. The follicular tissue that remains in the ovary after ovulation is transformed into the corpus luteum, an endocrine tissue that secretes female hormones during what is called the luteal phase of the ovarian cycle. The next cycle begins with a new growth of follicles.

Contraception literally means "against taking," in this case, the taking in of a child. The term has come to mean preventing a pregnancy through one of several methods. These methods fall into three main categories: (1) preventing the egg and sperm from meeting in the female reproductive tract, (2) preventing implantation of a zygote, and (3) preventing the release of mature eggs and sperm from the gonads.

Besides complete abstinence, the methods that prevent release of gametes are the most effective means of birth control. Chemical contraception (birth control pills) have failure rates of less than 1%, and sterilization is nearly 100% effective. Birth control pills are combinations of a synthetic estrogen and a synthetic progestin (progesterone-like hormone). These two hormones act by negative feedback to stop the release of GnRH by the hypothalamus and FSH (an estrogen effect) and LH (a progestin effect) by the pituitary. By blocking LH release, the progestin prevents ovulation. As a backup measure, the estrogen inhibits FSH secretion so no follicles develop. Chemical contraception has been the center of much debate, particularly because of the long-term side effects of the estrogens. No solid evidence exists for cancers caused by the pill, but cardiovascular problems are a major concern. Birth control pills have been implicated in blood clotting, atherosclerosis, and heart attacks. Smoking while using chemical contraception increases the risk of mortality tenfold or more. Campbell, N.; *Biology*, 2nd Ed., Benjamin/Cummings Publ., Redwood City, La., 1990.

Accordingly, there is a current need for inhibitors of MMPs. Such inhibitors would be useful to treat or prevent cancer, tumor metastasis, angiogenesis in tumors, contraception, arthritis and connective tissue diseases, cardiovascular disease, inflammation or autoimmune diseases. Preferred inhibitors may exhibit selectivity for one or more specific MMPs than known competitive inhibitors. In addition, additional methods that prevent the release of gametes are needed. Suth methods will preferably not include negative long-term side-effects.

SUMMARY OF THE INVENTION

The present invention provides compounds that inhibit MMPs. Accordingly, there is provided a compound of the invention which is a compound of formula (I):

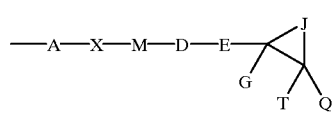

(I)

wherein
A—X—M is a hydrophobic group;
D is O, S, ($C_1$–$C_6$)alkyl, a direct bond, $SO_2$, SO, C(=O)NR, C(=O)O, NRC(=O), or OC(=O);
E is a direct bond, ($C_1$–$C_6$)alkyl, ($C_3$–$C_8$)cycloalkyl, ($C_2$–$C_6$)alkenyl, or ($C_2$–$C_6$)alkynyl, wherein any alkyl, cycloalkyl, alkenyl, or alkynyl of E is optionally substituted with one or more ($C_1$–$C_6$)alkyl, hydroxy, ($C_1$–$C_6$)alkoxy, cyano, nitro, halo, SR, NRR, or COOR, wherein each R is independently H or ($C_1$–$C_6$)alkyl;
J is S or O;
G, T, and Q are each independently H, ($C_1$–$C_6$)alkyl, or cyano;
or a pharmaceutically acceptable salt thereof.

The present invention also provides a pharmaceutical composition that comprises a compound of formula (I) and a pharmaceutically acceptable carrier.

The present invention also provides a radiolabeled compound comprising a compound of formula (I) and a radionuclide.

The present invention also provides a pharmaceutical composition that comprises a radiolabeled compound of formula (J) and a pharmaceutically acceptable carrier.

The present invention also provides a therapeutic method for preventing or treating a pathological condition or symptom in a mammal, such as a human, wherein the activity of an MMP is implicated and inhibition of its action is desired, comprising administering to a mammal in need of such therapy, an effective amount of a compound of formula (I), or a pharmaceutically acceptable salt thereof.

The present invention also provides a method for treating or preventing cancer, angiogenesis, arthritis, connective tissue disease, cardiovascular disease, inflammation or autoimmune disease in a mammal inflicted with or at risk thereof comprising administering to the mammal in need of such treatment or prevention an effective amount of a compound of formula (I).

The present invention also provides a method for treating or preventing cancer in a mammal inflicted with or at risk thereof comprising administering to the mammal in need of such therapy an effective amount of a compound of formula (I), or a pharmaceutically acceptable salt thereof in conjunction with a chemotherapeutic agent, or a pharmaceutically acceptable salt thereof.

The present invention also provides a method for inhibiting a matrix metalloproteinase comprising a zinc atom, the method comprising contacting the matrix metalloproteinase with a compound with a group that can be activated for nucleophilic substitution by the zinc atom and can form a covalent bond with a nucleophile of the matrix metalloproteinase.

The present invention also provides a method for inhibiting a gelatinase comprising a zinc atom, the method comprising contacting the gelatinase with a compound with a group that can be activated for nucleophilic substitution by the zinc atom and can form a covalent bond with a nucleophilic site of the gelatinase.

The present invention also provides a method for imaging a tumor in a mammal inflicted with a tumor comprising administering to the mammal an effective amount of a radiolabeled compound of formula (I), or a pharmaceutically acceptable salt thereof, and detecting the presence of the radiolabeled compound.

The present invention also provides a method to image MMP activity in a tumor and/or a vasculature comprising contacting the organism (e.g., in vivo) with an effective amount of a compound the present invention, wherein the compound of formula (I) comprises a radionuclide; or a pharmaceutically acceptable salt thereof.

The present invention also provides a method for imaging MMP activity in a tumor in a mammal inflicted with a tumor comprising administering to the mammal in need of such imaging an effective amount of a compound the present invention, wherein the compound of formula (I) comprises a radionuclide; or a pharmaceutically acceptable salt thereof.

The present invention also provides a method for preventing ovulation in a mammal (e.g., human) at risk thereof comprising administering to the mammal an effective amount of a compound of formula (I).

The present invention also provides a method for preventing the implantation of a fertilized egg into the uterus of a mammal (e.g., human) in need thereof comprising administering to the mammal an effective amount of a compound of formula (I).

DETAILED DESCRIPTION OF THE INVENTION

Figure 1:
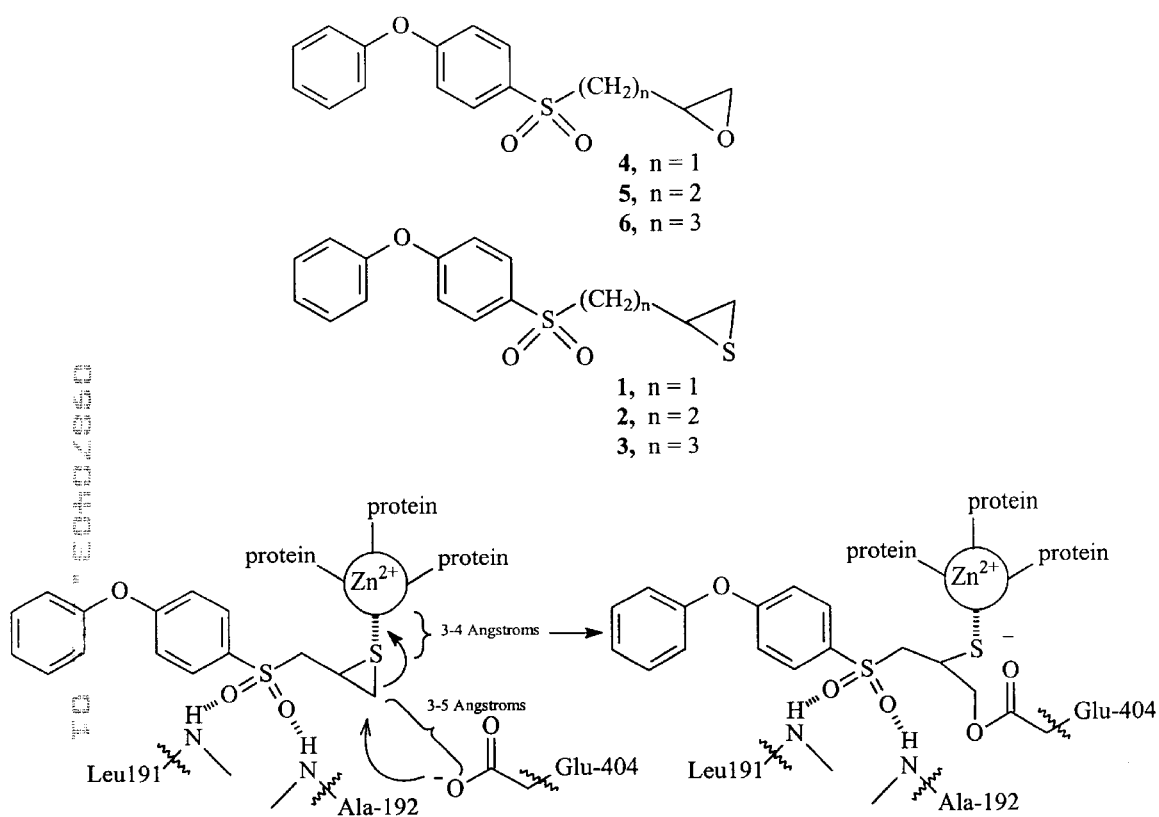
FIG. 1 illustrates a mechanism-based inhibition of an MMP by a compound of the present invention.

The following definitions are used, unless otherwise described: halo is fluoro, chloro, bromo, or iodo. Alkyl, alkoxy, alkenyl, alkynyl, etc. denote both straight and branched groups; but reference to an individual group such as "propyl" embraces only the straight chain variant, a branched chain isomer such as "isopropyl" being specifically referred to. Bicyclic aryl denotes an ortho-fused bicyclic carbocyclic substituent having about nine to ten ring atoms in which at least one ring is aromatic. Monocyclic heteroaryl encompasses a substituent attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl. Bicyclic heteroaryl encompasses a substituent of an ortho-fused bicyclic heterocycle of about eight to ten ring atoms derived therefrom, particularly a benzyl-derivative or one derived by fusing a propylene, trimethylene, or tetramethylene divalent substituent thereto. Bicyclic alkyl encompasses a substituent of an ortho-fused bicyclic alkyl of about eight to ten ring atoms containing five or six ring atoms consisting of carbon and one to four ring atoms consisting of heteroatoms selected from the group consisting of non-peroxide oxygen, sulfur, and N(X) wherein X is absent or is H, O $(C_1-C_4)$alkyl, phenyl or benzyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine MMP inhibition activity using the standard tests described hereinbelow, or using other similar tests which are well known in the art.

As used herein, "ovulation" is the release of an ovum from the ovarian follicle. Stedman's Medical Dictionary, 25th Ed., Illustrated, Williams & Wilkins, Baltimore, 1990, p.1116.

As used herein, "ovum" is the female sex (reproductive) cell. When fertlized by a spermatozoon, an ovum is capable of developing into a new individual of the same species. Stedman's Medical Dictionary, 25th Ed., Illustrated, Williams & Wilkins, Baltimore, 1990, p.1116.

As used herein, "fertiliziation" is the process beginning with penetration of the secondary oocyte by the spermatozoon and completed by infusion of the male and female pronuclei. Stedman's Medical Dictionary, 25th Ed., Illustrated, Williams & Wilkins, Baltimore, 1990, p.573.

As used herein, a "uterus" is the womb, metra, or the hollow muscular organ in which the impregnated ovum is developed into the child. Stedman's Medical Dictionary, 25th Ed., Illustrated, Williams & Wilkins, Baltimore, 1990, pp.1677–1678.

Specific and preferred values listed below for substituents (i.e., groups) and ranges are for illustration only; they do not exclude other defined values or other values within defined ranges for the substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_2-C_6)$alkanoyloxy can be acetoxy, propanoyloxy, butanoyloxy, isobutanoyloxy, pentanoyloxy, or hexanoyloxy; $(C_3-C_8)$cycloalkyl can be cyclopropyl, cyclobutyl, cyclopentyl, cyclohexyl, cycloheptyl, or cyclooctyl; aryl can be phenyl, indenyl, 5,6,7,8-tetrahydronaphthyl, or naphthyl and heteroaryl can be furyl, imidazolyl, tetrazolyl, pyridyl, (or its N-oxide), thienyl, pyrimidinyl (or its N-oxide), indolyl, or quinolyl (or its N-oxide); bicyclic aryl can be indenyl or naphthyl; monocyclic heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl (or its N-oxide), thienyl, or pyrimidinyl (or its N-oxide), bicyclic heteroaryl can be quinolyl (or its N-oxide); and bicyclic alkyl can be decahydroquinoline or decahydronaphthalene (cis and trans).

As used herein, an "amino acid" is a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; α-methyl-alanine; para-benzoylphenylalanine; phenylglycine; propargylglycine; sarcosine; and tert-butylglycine) residue having one or more open valences. The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a $(C_1-C_6)$alkyl, phenyl or benzyl ester or amide). Other suitable amino and carboxy protecting groups are known to those skilled in the art (See for example, T. W. Greene, *Protecting Groups In Organic Synthesis*; Wiley: New York, 1981; D. Voet, *Biochemistry*, Wiley: New York, 1990; L. Stryer, *Biochemistry*, (3rd Ed.), W.H. Freeman and Co.: New York, 1975; J. March, *Advanced Organic Chemistry Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein). According to the invention, the amino or carboxy protecting group can also comprise a radionuclide (e.g., Fluorine-18, Iodine-123, or Iodine-124).

As used herein, an "electrophile" refers to a chemical species, ion, or a portion of a compound which, in the course of a chemical reaction, will acquire electrons, or share electrons, to form other molecules or ions. Electrophiles are ordinarily thought of as cationic species (positively charged). *McGraw-Hill Concise Encyclopedia of Science & Technology*, McGraw-Hill, p.715, 4$^{th}$ Edition, NY, N.Y. (1998).

As used herein, a "nucleophile" refers to a chemical species, ion, or a portion of a compound which, in the course of a chemical reaction, will lose electrons, or share electrons, to form other molecules or ions. Nucleophiles are ordinarily thought of as anionic species (negatively charged). Typical nucleoplic species include, e.g., hydroxyl (OH), halo (F, Cl, Br, or I), cyano (CN), alkoxy ($CH_3CH_2O$), carboxyl (COO), and thio (S). *McGraw-Hill Concise Encyclopedia of Science & Technology*, McGraw-Hill, p.715, 4th Edition, NY, N.Y. (1998).

As used herein, a "peptide" is a sequence of 2 to 25 amino acids (e.g. as defined hereinabove) or peptidic residues having one or more open valences. The sequence may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, such as, for example, through the sulfur of a cysteine. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

As used herein, a "hydrophobic group" or "hydrophobic moiety" refers to a group that is relatively non-polar and will have a relatively minimal affinity for water. The nature of the hydrphobic group (i.e., A—X—M) is not important, provided the hydrophobic group fits into the pocket and has a favorable interaction (e.g., binding) with the enzyme. The hydrophobic group, while being relatively hydrophobic, can include one or more heteroatoms (e.g., S, O, or N) that can have an electrostatic charge or can include one or more groups (e.g., esters or amides) that can have an electrostatic charge, provided the hydrophobic group fits into the pocket and has a favorable interaction with the enzyme.

Any suitable hydrophobic group can be employed as A—X—M, provided the hydrophobic group fits into the pocket and has a favorable interaction (e.g., binding) with the enzyme. For example, the hydrophobic group can include a straight-chained or branched hydrocarbon chain (e.g., alkyl, alkenyl, or alkynyl), an aryl group (e.g., monocyclic or bicylic), a heteroaryl group (e.g., monocyclic or bicylic), a cycloalkyl group, an amino acid, a peptide, or a combination thereof.

In one embodiment, A—X—M can be a saturated or partially unsaturated hydrocarbon chain comprising one or more carbon atoms and optionally comprising one or more oxy (—O—), thio (—S—), sulfinyl (—SO—), sulfonyl ($S(O)_2$—), or $NR_f$ in the chain, wherein each Rf is independently hydrogen or ($C_1$–$C_6$)alkyl. The saturated or partially unsaturated hydrocarbon chain can optionally be substituted with one or more oxo (=O), hydroxy, cyano, halo, nitro, trifluoromethyl, trifluoromethoxy, ($C_1$–$C_6$)alkyl, ($C_1$–$C_6$) alkoxy, ($C_1$–$C_6$)alkoxy($C_1$–$C_6$)alkyl, ($C_3$–$C_8$)cycloalkyl, aryl, heteroaryl, ($C_3$–$C_8$)cycloalkyl($C_1$–$C_6$)alkyl, (aryl) ($C_1$–$C_8$)alkyl, (heteroaryl)($C_1$–$C_6$)alkyl, ($C_3$–$C_8$)cycloalkyl oxy, (aryl)oxy, (heteroaryl)oxy, ($C_3$–$C_8$)cycloalkyl (aryl) oxy(aryl), (heteroaryl)oxy(heteroaryl), ($C_3$–$C_8$)cycloalkyl oxy ($C_1$–$C_6$)alkyl, (aryl)oxy ($C_1$–$C_6$)alkyl, or (heteroaryl) oxy ($C_1$–$C_6$)alkyl. In addition, any aryl, ($C_3$–$C_8$)cycloalkyl, or heteroaryl can optionally be substituted with one or more oxo (=O), hydroxy, cyano, halo, nitro, trifluoromethyl, trifluoromethoxy, ($C_1$–$C_6$)alkyl, ($C_1$–$C_6$)alkoxy, ($C_1$–$C_6$) alkoxy($C_1$–$C_6$)alkyl, ($C_3$–$C_8$)cycloalkyl, aryl, heteroaryl, ($C_3$–$C_8$)cycloalkyl($C_1$–$C_6$)alkyl, (aryl)($C_1$–$C_8$)alkyl, (heteroaryl)($C_1$–$C_6$)alkyl, ($C_3$–$C_8$)cycloalkyl oxy, (aryl)oxy, (heteroaryl)oxy, ($C_3$–$C_8$)cycloalkyl, (aryl)oxy(aryl), (heteroaryl)oxy(heteroaryl), ($C_3$–$C_8$)cycloalkyl oxy ($C_1$–$C_6$)alkyl, (aryl)oxy ($C_1$–$C_6$)alkyl, or (heteroaryl)oxy ($C_1$–$C_6$)alkyl.

When A—X—M is a "partially unsaturated" group, such group may comprise one or more (e.g. 1 or 2) carbon—carbon double or triple bonds. For example, when A—X—M is a partially unsaturated ($C_1$–$C_6$)alkyl, it can be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 2,4-hexadienyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 3-hexen-5-ynyl, 4-hexynyl, or 5-hexynyl.

A specific value for A—X—M is A and M are each independently phenyl or monocyclic heteroaryl, wherein any phenyl or heteroaryl is optionally substituted with one or more (e.g., 1, 2, 3, or 4) hydroxy, ($C_1$–$C_6$)alkyl, ($C_1$–$C_6$) alkanoyl, ($C_1$–$C_6$)alkanoyloxy, ($C_1$–$C_6$)alkoxy, cyano, nitro, halo, trifluoromethyl, trifluoromethoxy, SR, NRR, or COOR; and X is O S, SO, $SO_2$, C(=O)NR, C(=O)O, NRC(=O), OC(=O), NR, a direct bond, or ($C_1$–$C_6$)alkyl optionally substituted with one or more hydroxy, ($C_1$–$C_6$) alkoxy, cyano, nitro, halo, SR, NRR, or COOR.

Another specific value for A—X—M is bicyclic aryl (e.g., naphthyl), bicyclic heteroaryl, or bicyclic alkyl; wherein any aryl, heteroaryl or alkyl is optionally substituted with one or more (e.g., 1, 2, 3, or 4) hydroxy, ($C_1$–$C_6$)alkyl, ($C_1$–$C_6$) alkanoyl, ($C_1$–$C_6$)alkanoyloxy, ($C_1$–$C_6$)alkoxy, cyano, nitro, halo, trifluoromethyl, trifluoromethoxy, SR, NRR, or COOR;

wherein each R is independently H, ($C_1$–$C_6$)alkyl, phenyl, benzyl, or phenethyl.

A specific value for A is phenyl or monocyclic heteroaryl. Another specific value for A is phenyl.

A specific value for M is phenyl or monocyclic heteroaryl. Another specific value for M is phenyl.

A specific value for X is O, S, SO, $SO_2$, C(=O)NR, C(=O)O, NRC(=O), OC(=O), NR, a direct bond, or ($C_1$–$C_6$)alkyl. Another specific value for X is O.

Another specific value for A—X—M is:

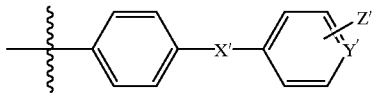

wherein

X' is O, ($C_1$–$C_6$)alkyl (e.g., $CH_2$), or a direct bond;

Y' is N or ($C_1$–$C_6$)alkyl (e.g., $CH_2$); and

Z' is halo, ($C_1$–$C_6$)alkoxy (e.g., $OCH_3$), or hydroxy.

Another specific value for A—X—M is:

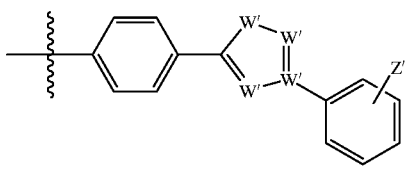

wherein
each W' is independently N or CH; and
Z' is halo, $(C_1-C_6)$alkoxy (e.g., $OCH_3$), or hydroxy.
Another specific value for A—X—M is:

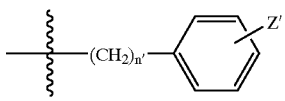

wherein
n' is about 1 to about 4; and
Z' is halo, $(C_1-C_6)$alkoxy (e.g., $OCH_3$), or hydroxy.
Another specific value for A—X—M is:

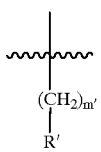

wherein
R' is O, $(C_1-C_6)$alkyl (e.g., $CH_2$), or S; and
m' is about 2 to about 7.
Another specific value for A—X—M is:

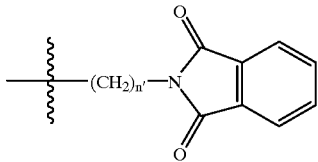

wherein
n' is about 1 to about 4.
Another specific value for A—X—M is:

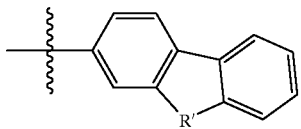

wherein
R' is O, $CH_2$, or S.
A specific value for D is $SO_2$.
A specific value for E is $(C_1-C_6)$alkyl. Another specific value for E is methyl.
A specific value for $(C_1-C_6)$alkyl is methyl.
A specific value for J is S.
A specific value for G is hydrogen.
A specific value for T is hydrogen.

A specific value for Q is hydrogen.
A specific compound of the present invention is a compound of formula (I) wherein A is phenyl, M is phenyl, X is O, D is $SO_2$, E is methyl, J is S, G is hydrogen, T is hydrogen, and Q is hydrogen.

Figure 2:
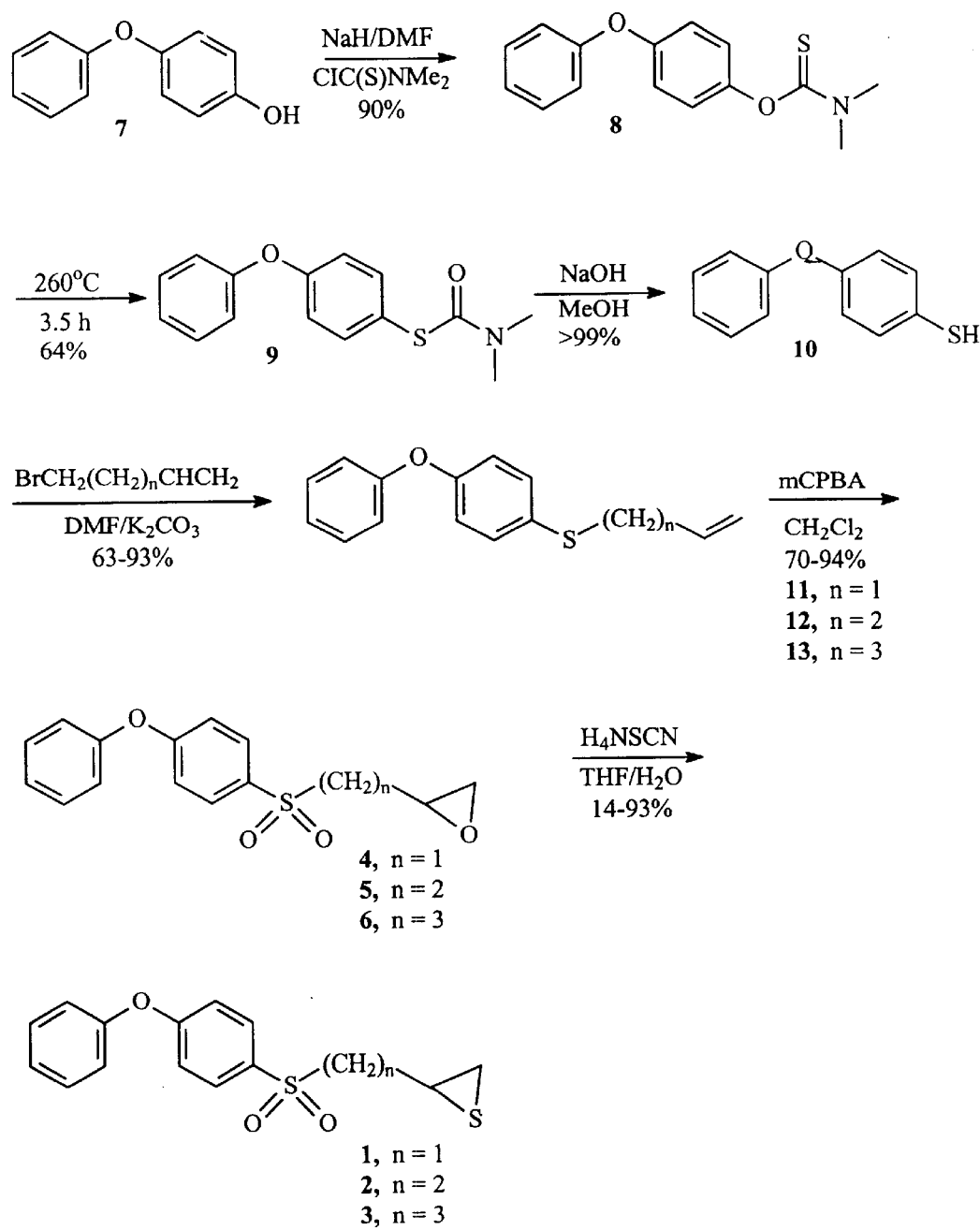
FIG. 2 illustrates a synthesis of compounds of the present invention.

FIG. 2 illustrates a synthesis for compounds 1–4. 4-phenoxythiophenol 10 was prepared from the commercially available 4-phenoxyphenol 7 via the 3 step procedure illustrated by Newman and Karnes. Newman M. S.; Kames H. A. *J. Org. Chem.*, 1996, 31, 3980–3984. Subsequent alkylation of 10 with allyl bromide, 4-bromo-1-butene and 5-bromo-1-pentene respectively, led to the sulfanyl compounds 11–13 in good yield. Although the epoxidation of 12 and 13 with mCPBA was relatively quick, taking only 2–3 days, the formation of 11 took 7 days and required a large excess of mCPBA. Finally, the conversion of the epoxides 4–6 to their corresponding thiirane derivatives 1–3, was accomplished via the treatment of each epoxide with ammoniumthiocyanate in THF/water. Although the thiiranes 2 and 3 were isolated in high yield, 93% and 85% respectively, thiirane 1 could only be recovered in a very poor (i.e., 14%) yield.

Processes for preparing compounds of formula (I) or for preparing intermediates useful for preparing compounds of formula (I) are provided as further embodiments of the invention. Intermediates useful for preparing compounds of formula (I) are also provided as further embodiments of the invention.

A compound of formula (I) wherein J is S can be prepared by treating a corresponding compound of formula (I) wherein J is O with a suitable sulfonating reagent. See, e.g., March, *Advanced Organic Chemistry, Reactions, Mechanisms and Structure*, $2^{nd}$ Ed., 1977 and Carey & Sundberg, *Advanced Organic Chemistry, Part B: Reactions*, $2^{nd}$ Ed., 1983.

A compound of formula (I) wherein J is O can be prepared by epoxidizing a corresponding compound of formula (I) wherein the ring that includes J is an alkene. See, e.g., March, *Advanced Organic Chemistry, Reactions, Mechanisms and Structure*, $2^{nd}$ Ed., 1977 and Carey & Sundberg, *Advanced Organic Chemistry, Part B: Reactions*, $2^{nd}$ Ed., 1983.

A compound of formula (I) wherein D is $SO_2$ and J is O can be prepared by oxidizing a corresponding compound of formula (I) wherein D is S. See, e.g., March, *Advanced Organic Chemistry, Reactions, Mechanisms and Structure*, $2^{nd}$ Ed., 1977 and Carey & Sundberg, *Advanced Organic Chemistry, Part B: Reactions*, $2^{nd}$ Ed., 1983.

A specific group of the compounds of the present invention, that can be activated by zinc for nucleophilic substitution and that can form a covalent bond with a nucleophile of the matrix metalloproteinase, includes a thiirane ring. Another specific group of the compounds of the present invention, that can be activated by zinc for nucleophilic substitution and that can form a covalent bond with a nucleophile of the matrix metalloproteinase, includes an oxirane ring. In addition, a specific nucleophile of the matrix metalloproteinase which can form a covalent bond with the group of the compounds of the present invention (e.g., thiirane or oxirane) is located at the amino acid residue corresponding to residue 404 of the matrix metalloproteinase, wherein the numbering is based on the active site general base for gelatinase A, which is observed in other MMPs. More specifically, the nucleophile is a carboxy (i.e., $COO^-$) oxygen atom located at amino acid residue corresponding to residue 404 of the matrix metalloproteinase, wherein the numbering is based on the active site general base for gelatinase A, which is observed in other MMPs. See, FIG. 1.

The matrix metalloproteinase can be a human matrix metalloproteinase. In addition, the matrix metalloproteinase can be a gelatinase, collagenase, stromelysin, membrane-type MMP, or matrilysin. Specifically, the gelatinase can be MMP-2 or MMP-9.

According to the method of the invention, the matrix metalloproteinase can be contacted with the compound, e.g., a compound of formula (I), in vitro. Alternatively, the matrix metalloproteinase can be contacted with the compound, e.g., a compound of formula (I), in vivo.

Without being bound by any particular theory, coordination of a thiirane in a compound of formula (I) with the enzyme active-site zinc ion is believed to activate the thiirane for modification by a nucleophile of the enzyme. See, FIG. 1. A computational model based on three-dimensional homology modeling for this enzyme with compound 1 indicates that the biphenyl group would fit in the active site analogously to the same group in certain known reversible inhibitors of MMP-2 and MMP-9, as analyzed by X-ray structure determination. Freskos, J. N.; Mischke B. V.; DeCrescenzo, G. A.; Heintz, R.; Getman, D. P.; Howard, S. C.; Kishore, N. N.; McDonald, J. J.; Munie, G. E.; Rangwala, S.; Swearingen, C. A.; Voliva, C.; Welsch, D. J. *Bioorg. & Med. Chem. Letters*, 1999, 9, 943–948. Tamura, Y.; Watanabe, F.; Nakatani, T.; Yasui, K.; Fuji, M.; Komurasaki, T.; Tsuzuki, H.; Maekawa, R.; Yoshioka, T.; Kawada, K.; Sugita, K.; Ohtani, M. *J. Med. Chem.* 1998, 41, 640–649. As such, the biphenyl ether moiety in compounds 1–4 is believed to fit in the P1' subsite of gelatinases, which is a deep hydrophobic pocket. (a) Morgunova, E.; Tuuttila, A.; Bergmann, U.; Isupov, M.; Lindqvist, Y.; Schneider, G.; Tryggvason, K. *Science* 1999, 284, 1667–1670. (b) Massova, I.; Fridman, R.; Mobashery, S. *J. Mol. Mod.* 1997, 3, 17–34; Olson, M. W.; Bernardo, M. M.; Pietila, M.; Gervasi, D. C.; Toth, M.; Kotra, L. P.; Massova, I.; Mobashery, S.; Fridman, R. *J. Biol. Chem.,* 2000, 275, 2661–2668. This binding mode brings the sulfur of the thiirane in 1 into the coordination sphere of the zinc ion. See, FIG. 1. The models also indicated that the thiirane moiety in compounds 2 and 3, with longer carbon backbones, would not be able to coordinate with the zinc ion as well as compound 1, but would fit in an extended configuration in the active site.

It is believed that the high specificity of certain compounds of the invention for a targeted enzyme arises predominantly from three factors. (i) the compounds satisfy the binding specificity requirements at the active site. In this respect these compounds are not any different from conventional reversible or affinity inhibitors. (ii) Furthermore, the structural features of the inhibition should allow it to undergo chemical activation by the zinc atom of the enzyme to generate an electrophilic species within the active site. (iii) Finally, there should be a nucleophilic amino-acid residue in the active site, in the proper orientation, to react with the electrophilic species (e.g., thiirane ring), resulting in irreversible enzyme inactivation.

By selecting a hydrophobic group (e.g., A—X—M) located a specific distance from a group (e.g., D) that can bind (e.g., hydrogen bond) with one or more sites in the enzyme (e.g., amino acid residue 191 and/or amino acid residue 192, in gelatinase A), which is in turn located a specific distance from a thiirane ring that can coordinate with the enzyme active-site zinc atom, one can prepare selective mechanism-based inhibitors for a given MMP. See, FIG. 1.

Accordingly, preferred MMP inhibitors have a hydrophobic aryl moiety (e.g., A—X—M) that can fit in the deep hydrophobic pocket (i.e., $P_1'$ subsite) of an MMP. In addition, preferred mechanism-based MMP inhibitors also have a thiirane ring that can coordinate with the enzyme active-site zinc ion, and be modified by a nucleophile (e.g., carboxylate group of amino acid residue 404 of MMP-2) in the enzyme active site. See, FIG. 1. The preferred MMP inhibitors can optionally include a second group (e.g., D) that can coordinate with one or more sites in the enzyme. Specifically, the second group can optionally hydrogen bond to the one or two proton donors (e.g., amino acid residue corresponding to residue 191 and/or amino acid residue corresponding to residue 192 of MMP-2) in the enzyme active site. See, FIG. 1.

The present invention provides a method for identifying a mechanistic based MMP inhibitor. The method includes providing a compound wherein (1) a hydrophobic moiety of the compound fits into a hydrophobic pocket of the MMP; (2) the compound has one or two groups that can hydrogen bond with one or two hydrogen donors of the MMP, wherein the hydrogen donors of the MMP are located at amino acid residue corresponding to residue 191 and amino acid residue corresponding to residue 192 of MMP-2; (3) the compound has an electrophilic group that can covalently bond with a nucleophile of the MMP, wherein the nucleophile of the MMP is located at amino acid residue corresponding to residue 404 of MMP-2; and/or (4) the compound includes a group that can coordinate with the zinc ion of the MMP.

Figure 3:
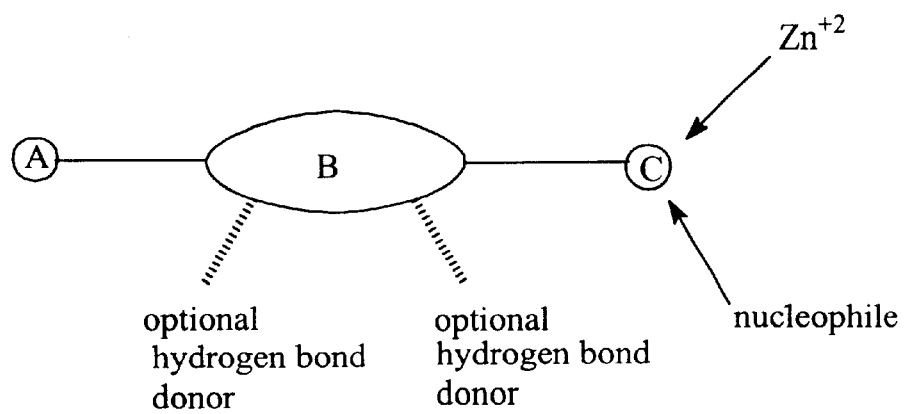
FIG. 3 illustrates a mechanism-based inhibition of an MMP by a compound of the present invention.

Preferred MMP inhibitors have a thiirane or oxirane such that the sulfur or oxygen atom of the thiirane or oxirane is located about 3 angstroms to about 4 angstroms from the zinc ion. The suitable MMP inhibitors can also include a thiirane or oxirane ring located about 3 angstroms to about 5 angstroms from the active site nucleophile. See, FIGS. 1 and 3.

Radiolabeled compounds of formula (I) are also useful as imaging agents for imaging cells comprising MMP's. Accordingly, the invention also provides compounds of formula (I) that include one or more detectable radionuclides (e.g., one or more metallic radionuclide and/or one or more non-metallic radionuclides). For example, a detectable radionuclide can be incorporated into a compound by replacing an atom of the compound of formula (I) with a radionuclide (e.g., non-metallic radionuclide). Alternatively, a radiolabeled compound of the invention can be prepared by linking a compound of formula (I) to a chelating group that includes a detectable radionuclide (e.g., metallic radionuclide). Such compounds can be useful to image tissues with MMP activity or tumors, in vivo or in vitro.

As used herein, a "chelating group" is a group that can include a detectable radionuclide (e.g., a metallic radioisotope). Any suitable chelating group can be employed. Suitable chelating groups are disclosed, e.g., in Poster Sessions, Proceedings of the 46th Annual Meeting, *J. Nuc.Med.,* p. 316, No. 1386; Scientific Papers, Proceedings of the 46th Annual Meeting, *J. Nuc.Med.,* p. 123, No. 499; Scientific Papers, Proceedings of the 46th Annual Meeting, *J. Nuc.Med.,* p. 102, No. 413; Scientific Papers, Proceedings of the 46th Annual Meeting, *J. Nuc.Med.,* p. 102, No. 414; Scientific Papers, Proceedings of the 46th Annual Meeting, *J. Nuc.Med.,* p. 103, No. 415; Poster Sessions, Proceedings of the 46th Annual Meeting, *J. Nuc.Med.,* p. 318, No. 1396; Poster Sessions, Proceedings of the 46th Annual Meeting, *J. Nuc.Med.,* p. 319, No. 1398; M. Moi et al., J. Amer. Chem., Soc., 49, 2639 (1989); S. V. Deshpande et al., J. Nucl. Med., 31, 473 (1990); G. Kuser et al., Bioconj. Chem., 1, 345

(1990); C. J. Broan et al., J. C. S. Chem. Comm., 23, 1739 (1990); C. J. Anderson et al., J. Nucl. Med. 36, 850 (1995); U.S. Pat. No. 5,739,313; and U.S. Pat. No. 6,004,533. Specifically, the chelating group can be.

As used herein, a "detectable radionuclide" is any suitable radionuclide (i.e., radioisotope) useful in a diagnostic procedure in vivo or in vitro. Suitable detectable radionuclides include metallic radionuclides (i.e., metallic radioisotopes) and non-metallic radionuclides (i.e., non-metallic radioisotopes).

Suitable metallic radionuclides (i.e., metallic radioisotopes or metallic paramagnetic ions) include Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gold-195, Gold-199, Hafnium-175, Hafnium-175–181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95.

Specifically, the chelating group can include more than one metallic radioisotope. More specifically, the detectable chelating group can include 2 to about 10, 2 to about 8, 2 to about 6, or 2 to about 4 metallic radioisotopes.

Specifically, the non-metallic radionuclide can be a non-metallic paramagnetic atom (e.g., Fluorine-19); or a non-metallic positron emitting radionuclide (e.g., Carbon-11, Fluorine-18, Iodine-123, or Bromine-76).

Specifically, the compounds of the present invention can include more than one non-metallic radioisotope. More specifically, the compounds of the present invention can include 2 to about 10, 2 to about 8, 2 to about 6, or 2 to about 4 non-metallic radioisotopes.

A compound of formula (I), or a pharmaceutically acceptable salt thereof, can be administered to a mammal (e.g., human) in conjunction with a chemotherapeutic agent, or a pharmaceutically acceptable salt thereof. Accordingly, a compounds of formula (I) can be administered in conjunction with a chemotherapeutic agent to treat a tumor or cancer.

As used herein, a "chemotherapeutic agent" is a compound that has biological activity against one or more forms of cancer and can be administered to a patient with a compound of formula (I) without losing its anticancer activity. Suitable chemotherapeutic agents include, e.g., antineoplasts. Representative antineoplasts include, e.g., adjuncts, androgen inhibitors, antibiotic derivatives, antiestrogens, antimetabolites, cytotoxic agents, hormones, immunomodulators, nitrogen mustard derivatives and steroids. Physicians' Desk Reference, 50th Edition, 1996.

Representative adjuncts include, e.g., levamisole, gallium nitrate, granisetron, sargramostim strontium-89 chloride, filgrastim, pilocarpine, dexrazoxane, and ondansetron. Physicians' Desk Reference, 50th Edition, 1996.

Representative androgen inhibitors include, e.g., flutamide and leuprolide acetate. Physicians' Desk Reference, 50th Edition, 1996.

Representative antibiotic derivatives include, e.g., doxorubicin, bleomycin sulfate, daunorubicin, dactinomycin, and idarubicin.

Representative antiestrogens include, e.g., tamoxifen citrate and analogs thereof. Physicians' Desk Reference, 50th Edition, 1996. Additional antiestrogens include nonsteroidal antiestrogens such as toremifene, droloxifene and roloxifene. Magarian et al., Current Medicinal Chemistry, 1994, Vol. 1, No. 1.

Representative antimetabolites include, e.g., fluorouracil, fludarabine phosphate, floxuridine, interferon alfa-2b recombinant, methotrexate sodium, plicamycin, mercaptopurine, and thioguanine. Physicians' Desk Reference, 50th Edition, 1996.

Representative cytotoxic agents include, e.g., doxorubicin, carmustine [BCNU], lomustine [CCNU], cytarabine USP, cyclophosphamide, estramucine phosphate sodium, altretamine, hydroxyurea, ifosfamide, procarbazine, mitomycin, busulfan, cyclophosphamide, mitoxantrone, carboplati, cisplati, cisplatin, interferon alfa-2a recombinant, paclitaxel, teniposide, and streptozoci. Physicians' Desk Reference, 50th Edition, 1996.

Representative hormones include, e.g., medroxyprogesterone acetate, estradiol, megestrol acetate, octreotide acetate, diethylstilbestrol diphosphate, testolactone, and goserelin acetate. Physicians' Desk Reference, 50th Edition, 1996.

Representative immunodilators include, e.g., aldesleukin. Physicians' Desk Reference, 50th Edition, 1996.

Representative nitrogen mustard derivatives include, e.g., melphalan, chlorambucil, mechlorethamine, and thiotepa. Physicians' Desk Reference, 50th Edition, 1996.

Representative steroids include, e.g., betamethasone sodium phosphate and betamethasone acetate. Physicians' Desk Reference, 50th Edition, 1996.

Additional suitable chemotherapeutic agents include, e.g., alkylating agents, antimitotic agents, plant alkaloids, biologicals, topoisomerase I inhibitors, topoisomerase II inhibitors, synthetics, antiangiogenic drugs, and antibodies. See, e.g., AntiCancer Agents by Mechanism, http://www.dtp.nci.nih.gov/docs/cancer/searches/standard_mechanism_list.html, Apr. 12, 1999; Approved Anti-Cancer Agents, http://www.ctep.info.nih.gov/handbook/HandBookText/fda_agen.htm, pages 1–7, Jun. 18, 1999; MCMP 611 Chemotherapeutic Drugs to Know, http//www.vet.purdue.edu/depts/bms/courses/mcmp611/chrx/drg2no61.html, Jun. 24, 1999; Chemotherapy, http://www.vetmed.1su.edu/oncology/Chemotherapy.htm, Apr. 12, 1999; and Angiogenesis Inhibitors in Clinical Trials, http://www.cancertrials.nci.nih.gov/news/angio/table.html, pages 1–5, Apr. 19, 2000.

Representative alkylating agents include, e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864. *AntiCancer Agents by Mechanism*, http://dtp.nci.nih.gov/docs/cancer/searches/standard_mechanism list.html, Apr. 12, 1999.

Representative antimitotic agents include, e.g., allocolchicine, Halichondrin B, colchicine, colchicine derivatives, dolastatin 10, maytansine, rhizoxin, paclitaxel derivatives, paclitaxel, thiocolchicine, trityl cysteine, vinblastine sulfate, and vincristine sulfate. *AntiCancer Agents by Mechanism*, http://dtp.nci.nih.gov/docs/cancer/searches/standard_mechanism_list.html, Apr. 12, 1999.

Representative plant alkaloids include, e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere. *Approved Anti-Cancer Agents*, http://ctep.info.nih.gov/handbook/HandBookText/fda_agent.htm, Jun. 18, 1999.

Representative biologicals include, e.g., alpha interferon, BCG, G-CSF, GM-CSF, and interleukin-2. *Approved Anti-Cancer Agents*, http://ctep.info.nih.gov/handbook/HandBookText/fda_agent.htm, Jun. 18, 1999.

Representative antiangiogenic drugs include e.g., marimastat, AG3340, COL-3, neovastat, BMS-275291, TNP-470, thalidomide, squalamine, combretastatin A-4 prodrug, endostatin, SU5416, SU6668, interferon-alpha, anti-VEGF antibody, EMD121974, CAI, interleukin-12, and IM862. *Angiogenesis Inhibitors in Clinical Trials*, http://www.cancertrials.nci.nih.gov/news/angio/table.html, pages 1–5, Apr. 19, 2000.

Representative topoisomerase I inhibitors include, e.g., camptothecin, camptothecin derivatives, and morpholinodoxorubicin. *AntiCancer Agents by Mechanism*, http://dtp.nci.nih.gov/docs/cancer/searches/standard_mechanism_list. html, Apr. 12, 1999.

Additional biologicals include drugs designed to inhibit tumor vascularization, which is also known as tumor angiogenesis. These drugs can be potent antiangiogenic agents. Additional biologicals include humanized antibodies to growth factors, for example, to HER2, signaling molecules and adhesion receptors. Additional biologicals also include treatment with recombinant viruses and other means of gene therapy delivery, including for example, DNA, oligonucleotides, rybozymes, and liposomes.

Representative topoisomerase II inhibitors include, e.g., mitoxantron, amonafide, m-AMSA, anthrapyrazole derivatives, pyrazoloacridine, bisantrene HCL, daunorubicin, deoxydoxorubicin, menogaril, N, N-dibenzyl daunomycin, oxanthrazole, rubidazone, VM-26 and VP-16. *AntiCancer Agents by Mechanism*, http://dtp.nci.nih.gov/docs/cancer/searches/standard_mechanism_list.html, Apr. 12, 1999.

Representative synthetics include, e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium. *Approved Anti-Cancer Agents*, http://ctep.info.nih. gov/handbook/HandBookText/fda_agen.htm, Jun. 18, 1999.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (e.g., sodium, potassium or lithium) or alkaline earth metal (e.g., calcium) salts of carboxylic acids can also be made.

The compounds of formula (I) can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (e.g., glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to act as an MMP inhibitor may be determined using pharmacological models which are well known to the art, or using the methods described hereinbelow.

Fluorescence Enzymatic Activity Assays

The enzymatic activity of MMP-2, MMP-9, and MMP-7 was monitored with the fluorescence quenched substrate MOCAcPLGLA$_2$pr(Dnp)-AR-NH$_2$. Fluorescence was measured with a Photon Technology International (PTI) spectrofluorometer interfaced to a Pentium computer, equipped with the RatioMaster™ and FeliX™ hardware and software, respectively. The cuvette compartment was thermostated at 25.0° C. Substrate hydrolysis was monitored at emission and excitation wavelengths of 328 and 393 nm and excitation and emission band passes of 1 and 3 nm, respectively. Fluorescence measurements were taken every 4 s. Less than 10% hydrolysis of the fluorogenic substrate was monitored, as described by Knight. Knight, C. G. *Methods Enzymol.* 1995, 248, 18–34. Stromelysin 1 enzymatic activity was monitored using the synthetic fluorogenic substrate MOCAcRPKPVE-Nva-WRK(Dnp)-NH$_2$ (Peptides International, Louisville, Ky.) at excitation and emission wavelengths of 325 and 393 nm and excitation and emission band passes of 1 and 3 nm, respectively.

Enzymes and Protein Inhibitors.

Human pro-MMP-2, pro-MMP-9, TIMP-1 and TIMP-2 were expressed in HeLa S3 cells infected with the appropriate recombinant vaccinia viruses and were purified to homogeneity, as previously described. Fridman, R.; Fuerst, T. R.; Bird, R. E.; Hoyhtya, M.; Oelkuct, M.; Kraus, S.; Komarek, D.; Liotta, L. A.; Berman, M. L.; Stetler-Stevenson, W. G. *J. Biol. Chem.* 1992, 267, 15398–15405. Fridman, R.; Birs, R. E.; Hoyhtya, M.; Oelkuct, M.;

Komarek, D.; Liang, C. M.; Berman, M. L.; Liotta, L. A.; Stetler-Stevenson, W. G.,; Fuerst, T. R. *Biochem. J.* 1993, 289, 411–416. Pro-MMP-2, pro-MMP-9, TIMP-1 and TIMP-2 concentrations were determined using the extinction coefficients of 122,800, 114,360, 26,500 and 39,600 $M^{-1}cm^{-1}$, respectively. To obtain active MMP-2, pro-MMP-2 (7.3 $\mu$M) was incubated at 37° C. for 1 h with 1 mM p-aminophenylmercuric acetate (APMA) (dissolved in 200 mM Tris) in buffer C. The enzyme solution was dialyzed against buffer D at 4° C. to remove APMA. Active MMP-9 was obtained by incubating pro-MMP-9 (1 $\mu$M) with heat-activated recombinant human stromelysin 1 (68 nM) (MMP-3, generously provided by Dr. Paul Cannon, Center for Bone and Joint Research, Palo Alto, Calif.) at 37° C., for 2.5 h in buffer C.

The resulting solution was subjected to gelatin-agarose chromatography to remove stromelysin 1. MMP-9 was eluted with buffer D containing 10% DMSO and dialyzed against the same buffer without DMSO to remove the organic solvent. Pro-MMP-2 and pro-MMP-9 activation reactions were monitored using the fluorescence quenched substrate MOCAcPLGLA$_2$pr(Dnp)-AR-NH$_2$ (Peptides International, Louisville, Ky.), as will be described below. The MMP-2 and MMP-9 concentrations were determined by titration with TIMP-1.

Kinetic Analyses.

Progress curves were obtained by adding enzyme (0.5–2 nM) to a mixture of fluorogenic substrate (5–7 $\mu$M) and varying concentrations of inhibitor in buffer R containing 5–15% DMSO (final volume 2 ml), in acrylic cuvettes with stirring and monitoring the increase in fluorescence with time for 15–30 minutes. The progress curves were nonlinear least squares fitted to Equation 1 (Muller-Steffner, H. M., Malver, O., Hosie, L., Oppenheimer, N. J., and Schuber, F. *J. Biol. Chem.* 1992, 267, 9606–9611.):

$$F = v_s t + I(v_o - v_s)(1 - exp(-kt))/k + F_0 \qquad (1)$$

where $v_o$ represents the initial rate, $v_s$, the steady state rate, k, the apparent first order rate constant characterizing the formation of the steady-state enzyme-inhibitor complex and $F_o$, the initial fluorescence, using the program SCIENTIST (MicroMath Scientific Software, Salt Lake City, Utah). The obtained k values, $v_0$ and $v_s$ were further analyzed according to Equations 2 and 3 for a one-step association mechanism $$k = k_{off} + k_{on}[I]/(1 + [S]/Km) \qquad (2)$$

$$(v_o - v_s)/v_s = [I]/(K_i(1 + [S]/K_m)) \qquad (3)$$

Intercept and slope values, obtained by linear regression of the k versus inhibitor concentration plot (Equation 2), yielded the association and dissociation rate constants $k_{on}$ and $k_{off}$, respectively, and the inhibition constant $K_i$ ($k_{off}/k_{on}$). Alternatively, $K_i$ was determined from the slope of the $(v_o - v_s)/v_s$ vs [I] plot according to Equation 3.

The dissociation rate constants were determined independently from the enzyme activity recovered after dilution of a pre-formed enzyme-inhibitor complex. To this end, typically 200 nM of enzyme was incubated with 1 $\mu$M of inhibitor for a sufficient time to reach equilibrium (>45 min) at 25.0° C. The complex was diluted into 2 mL of buffer R containing fluorogenic substrate (5–7 $\mu$M final concentration) to a final enzyme concentration of 1 nM. Recovery of enzyme activity was monitored for ~30 min. The fluorescence versus time trace was fitted, using the program SCIENTIST, to Equation 4

$$F = v_s t + (v_o - v_s)(1 - exp(-k_{off}))/k_{off} + F_0 \qquad (4)$$

where $v_o$ represents the initial rate (very small), $v_s$, the rate observed when the E.I complex is completely dissociated and $k_{off}$, the first order rate constant when the E.I dissociation.

Analysis for linear competitive inhibition was performed in the following manner. Initial rates were obtained by adding enzyme (0.5–2 nM) to a mixture of fluorogenic substrate (5–7 $\mu$M) and varying concentrations of inhibitor in buffer R, containing 5–15% DMSO (final volume 1 mL) in semi-micro quartz cuvettes, and monitoring the increase in fluorescence with time for 5–10 minutes. The fluorescence versus time traces were fitted by linear regression analysis using FeliX™. The initial rates were fitted to Equation 5 (Segel, I. H. in: *Enzyme Kinetics*, Wiley Inc., New York, 1975, pp. 104.):

$$v/V_{max} = S/(K_m(1 + I/K_i) + S) \qquad (5)$$

where v and $V_{max}$ represent the initial and maximal velocities, S and I, the substrate and inhibitor concentrations, respectively, $K_m$ the Michaelis-Menten constant for the substrate-enzyme reaction and $K_i$ the inhibition constant, using the program SCIENTIST.

Inhibitors 1–4 all bind with the active site of the MMPs that were used in the study, with $K_i$ values of micromolar, or less, however, the behavior of inhibitor 1 was very different. Inhibitor 1 showed a dual behavior. It served as a mechanism-based inhibitor with a partition ratio of 79±10 (i.e. $k_{cat}/k_{inact}$) for MMP-2 and 416±63 for MMP-9. Furthermore, it also behaved as a slow-binding inhibitor, for which the rate constants for the on-set of inhibition ($k_{on}$) and recovery of activity from inhibition ($k_{off}$) were evaluated (Table 1). It would appear that coordination of the thiirane with the zinc ion (as seen in energy-minimized computational models; FIG. 1) would set in motion a conformational change, which is presumed from the slow-binding kinetic behavior. The kinetic data fit the model for slow-binding inhibition. Morrison, J. F. *Adv. Enzymol.* 1988, 61, 201–301. Covalent modification of the enzymes results from this conformational change. Inhibitor 1 was incubated with MMP-2 to the point that less than 5% activity remained. This inhibitor-enzyme complex was dialyzed over three days, which resulted in recovery of approximately 50% of the activity. This observation is consistent with modification of the active site Glu-404 (according to the numbering for human MMP-2), via the formation of an ester bond, which is a relatively labile covalent linkage. The time-dependent loss of activity is not merely due to the slow-binding behavior. For instance, for a $k_{off}$ of $2 \times 10^{-3}$ s$^{-1}$ (the values are not very different from one another in Table 1) the half time for recovery of activity ($t_{1/2}$) is calculated at just under 6 min. The fact that 50% of activity still did not recover after dialysis over three days strongly argues for the covalency of enzyme modification.

Selectivity in inhibition of gelatinases by inhibitor 1 was observed. Its $K_i$ values are 13.9±4 nM and 600±200 nM for MMP-2 and MMP-9, respectively. The corresponding $K_i$ values are elevated to the micromolar range for the other MMPs, even for the case of MMP-3, which does show the slow-binding, mechanism-based inhibition profile. In addition, the values for $k_{on}$ are 611- and 78-fold larger for MMP-2 and MMP-9, respectively, than that for MMP-3. Whereas the $k_{off}$ values are more similar to one another, the value for MMP-2 is the smallest, so the reversal of inhibition of this enzyme takes place more slowly. Collectively, these kinetic parameters demonstrate that inhibitor 1 can be a potent and selective inhibitor for MMP-2, MMP-9, and especially MMP-2. It has been previously shown that two molecules of either TIMP-1 or TIMP-2 (endogenous cellular protein inhibitors of MMPs) bind to activated MMP-2 and MMP-9. Olson, M. W.; Gervasi, D. C.; Mobashery, S.; Fridman, R. *J. Biol. Chem.* 1997, 272, 29975. One binding event is high affinity and would appear physiologically relevant, whereas the second binding event takes place with relatively lower affinity (micromolar). Olson, M. W.; Gervasi, D. C.; Mobashery, S.; Fridman, R. *J. Biol. Chem.* 1997, 272, 29975. Inhibition of MMP-2 and MMP-9 by TIMPs also follows slow-binding kinetics. The kinetic parameters for these interactions at the high affinity site are listed in Table 1. The kinetic parameters for the slow-binding component of inhibition of MMP-2 and MMP-9 by inhibitor 1 ($K_{on}$ and $K_{off}$) approach closely the same parameters for those of the protein inhibitors. Olson, M. W.; Gervasi, D. C.; Mobashery, S.; Fridman, R. *J. Biol. Chem.* 1997, 272, 29975–29983.

Oxiranes 4–6 inhibit MMPs in a competitive manner with higher $K_i$ values. There was no evidence of slow-binding behavior or time-dependence of loss of activity with this inhibitor with any of the MMPs.

Small-molecule inhibitor 1 follows both slow-binding and mechanism-based inhibition in its kinetic profile. This compound appears to behave very similarly to the endogenous cellular protein inhibitors for MMPs (TIMPs) in the slow-binding component of inhibition. Furthermore, the inhibitor also exhibits a covalent mechanism-based behavior in inhibition of these enzymes. The high discrimination in targeting that inhibitor 1 displays (both in affinities and the modes of inhibition) among the other structurally similar MMPs is noteworthy and could serve as a paradigm in the design of inhibitors for other closely related enzymes in the future.

EXAMPLES

Experimental Procedures $^1$H and $^{13}$C NMR spectra were recorded on either a Varian Gemini-300, a Varian Mercury-400 or a Varian Unity-500 spectrometer. Chemical shifts are reported in ppm from tetramethylsilane on the δ scale. Infrared spectra were recorded on a Nicolet 680 DSP spectrophotometer. Mass spectra were recorded on a Kratos MS 8ORFT spectrometer. Melting points were taken on an Electrothermal melting point apparatus and are uncorrected. Thin-layer chromatography was performed with Whatman reagents 0.25 mm silica gel 60-F plates. All other reagents were purchased from either Aldrich Chemical Company or Across Organics.

The following buffers were used in experiments with enzymes: Buffer C (50 mM HEPES at pH 7.5, 150 mM NaCl, 5 mM CaCl$_2$, 0.02% Brij-35); buffer R (50 mM HEPES at pH 7.5, 150 mM NaCl, 5 mM CaCl$_2$, 0.01% Brij-35, and 1% v/v Me$_2$SO) and buffer D (50 mM Tris at pH 7.5, 150 mM NaCl, 5 mM CaCl$_2$, and 0.02% Brij-35).

Example 1

(4-Phenoxyphenylsulfonyl)methyloxirane (4).

To compound 11 (598 mg, 2.5 mmol) in dichloromethane (10 mL), mCPBA (2.84 g, 10 mmol, Aldrich 57–86%), was slowly added. The mixture was stirred at room temperature for 3 days, after which time a second portion of mCPBA (2.84 g, 10 mmol) was added. The mixture was then stirred for another 4 days, after which time the mixture was poured into ethyl acetate (200 mL), and washed with aqueous sodium thiosulfate (3×50 mL, 10% w/v), aqueous sodium bicarbonate (3×50 ml, 5% w/v), and brine (50 ml). The organic phase was dried over magnesium sulfate and was concentrated to provide a yellow oil. The crude material was purified by column chromatography (silica, 4:1 hexanes:ethyl acetate) to give compound 4 as a pale yellow semi-solid (501 mg, 70%). $^1$H NMR (500 MHz, CDCl$_3$) δ 7.90–7.86 (m, 2H), 7.46–7.40 (m, 2H), 7.26–7.22 (m, 1H), 7.10–6.96 (m, 4H), 3.34–3.24 (m, 2H), 2.84–2.80 (m, 1H), 2.49–2.46 (m, 1H); $^{13}$C NMR (125 MHz, CDCl$_3$) δ 163.15, 154.95, 130.76, 130.51, 125.52, 120.77, 117.83, 59.89, 46.13; IR(film) 3054 (w), 2919 (w), 1576 (s), 1492 (s), 1320 (s), 1245 (s), 1148 (s) cm$^{-1}$; m/z (EI) 290 (M$^+$, 100%), 233 (70), 217 (50), 185 (40); HRMS (EI) calcd. for C$_{15}$H$_{14}$O$_4$S 290.0613, found 290.0611.

The intermediate, compound 11, was prepared as follows:

(A.) O-4-Phenoxyphenyl-N,N-dimethylthiocarbamate (8).

To a solution of 4-phenoxyphenol (7, 8.46 g, 45 mmol) in DMF (40 mL) at 10° C., sodium hydride (1.83 g, 45 mmol, 60% dispersion in mineral oil) was added in small portions. After the evolution of hydrogen ceased, N,N-dimethylthiocarbamoyl chloride (6.16 g, 50 mmol) was added in one portion. The reaction mixture was then stirred at 70° C. for 2 hours. The mixture was cooled to room temperature, poured into water (100 mL) and extracted with chloroform (3×50 mL). The combined organic extracts were washed with aqueous potassium hydroxide (50 mL, 5% w/v), and brine (10×50 mL). The organic extract was dried over magnesium sulfate and concentrated to obtain a yellow oil. The crude material was purified by column chromatography (silica, 5:1 hexanes:ethyl acetate) to give compound 8 as a white solid (11.16 g, 90%). m.p. 50–51° C.; $^1$H NMR (300 MHz, CDCl$_3$) δ 7.38–7.31 (m, 2H), 7.14–7.08 (m, 1H), 7.06–7.00 (m, 6H), 3.46 (s, 3H), 3.34 (s, 3H); $^{13}$C NMR (75 MHz, CDCl$_3$) δ 188.17, 157.26, 155.16, 149.62, 130.05, 124.11, 123.71, 119.31, 43.57, 38.96; IR (KBr) 3040 (m), 2938 (s), 1587 (s), 1487 (s), 1394 (s), 1287 (s), 1190 (s) cm$^{-1}$; m/z (EI) 273 (M$^+$, 15%), 186 (100); HRMS (EI) calcd. for C$_{15}$H$_5$NO$_2$S 273.0823, found 273.0824.

(B.) S-4-Phenoxyphenyl-N,N-dimethylthiocarbamate (9).

Compound 8 (3.99 g, 15 mmol) was heated under argon at 260° C. for 3.5 hours. The resulting dark brown oil was purified by column chromatography using a gradient eluent system (silica, 19:1 then 9:1 then 3:1 hexanes:ethyl acetate) to obtain compound 9 as a pale yellow solid (2.55 g, 64%). m.p. 97–99° C.; $^1$H NMR (400 MHz, CDCl$_3$) δ 7.45–7.40 (m, 2H), 7.40–7.30 (m, 2H), 7.15–7.10 (m, 1H), 7.05 (d, J=8.8 Hz, 2H) 6.98 (d, J=8.8 Hz, 2H) 3.08 (bs, 3H), 3.02 (bs, 3H); $^{13}$C NMR (100 MHz, CDCl$_3$) δ 167.48, 158.87, 156.53, 137.66, 130.09, 124.14, 122.39, 119.87, 118.94, 37.14; IR(KBr) 3037 (w), 2925 (w), 1652 (s), 1581 (s) 1486 (s), 1239 (s) cm$^{-1}$; m/z (EI) 273 (M$^+$, 25%), 257 (5), 200 (5); HRMS (EI) calcd. for C$_{15}$H$_{15}$NO$_2$S 273.0823, found 273.0822.

(C.) 4-Phenoxythiophenol (10).

A mixture of compound 9 (2.55 g, 9 mmol) in methanol (20 mL), and aqueous NaOH (10 mL, 10% w/v), were refluxed for 4 hours. The solution was cooled to room temperature and was acidified to pH 1 with aqueous HCl (1M). Water (100 mL) was added and the mixture was extracted with chloroform (3×50 mL). The combined organic extracts were washed with brine (50 mL), dried over magnesium sulfate and concentrated to obtain a yellow oil. The crude product was purified by column chromatography (silica, 5:1 hexanes:ethyl acetate) to give compound 10 as a pale yellow oil (1.80 g, >99%). 1H NMR (300 MHz, CDCl$_3$) δ 7.36–7.31 (m, 2H), 7.30–7.25 (m, 2H), 7.13–7.09 (m, 1H), 7.04–6.88 (m, 4H), 3.43 (s, 1H); $^{13}$C NMR (75 MHz, CDCl$_3$) δ 157.30, 156.15, 132.14, 130.00, 124.04, 123.95, 119.88, 119.04; IR(film) 3038 (w), 1583 (s), 1484 (s), 1236 (s), 1166 (s) cm$^{-1}$; m/z (EI) 202 (M$^+$, 100%); HRMS (EI) calcd. for C$_{12}$H$_{10}$OS 202.0452, found 202.0454.

(D.) 3-(4-Phenoxyphenylsulfanyl)-1-propene (11).

To a mixture of compound 10 (516 mg, 2.7 mmol) and potassium carbonate (534 mg, 3.9 mmol) in DMF (5 mL), allyl bromide (253 μL, 2.9 mmol) was added in one portion. The mixture was stirred at room temperature overnight. The crude reaction mixture was poured into ether (200 mL), washed with saturated aqueous potassium carbonate (25 mL), and brine (6×50 mL). The organic layer was dried over magnesium sulfate and concentrated in vacuo to give a yellow oil. The crude material was purified by column chromatography, (silica, 98:2 hexanes:ethyl acetate) to obtain the title compound as a pale yellow oil (598 mg, 93%). $^1$H NMR (300 MHz, CDCl$_3$) δ 7.38–7.32 (m, 4H), 7.15–7.10 (m, 1H), 7.04–7.00 (m, 2H), 6.97–6.92 (m, 2H), 5.92–5.82 (m, 1H), 5.10–5.04 (m, 2H), 3.50 (d, J=7.2 Hz, 2H); $^{13}$C NMR (75 MHz, CDCl$_3$) δ 157.14, 156.73, 134.01, 133.22, 130.05, 129.50, 123.75, 119.40, 119.25, 117.81, 38.84; IR(film) 3078 (w), 3039 (w), 1582 (s), 1484 (s), 1240 (s), 1165 (s) cm$^{-1}$; m/z (EI) 242 (M+, 100%), 201 ([M-allyl]$^+$, 100); HRMS (EI) calcd. for C$_{15}$H$_{14}$OS 242.0765, found 242.0764.

Example 2
2-(4-Phenoxyphenylsulfonyl)ethyloxirane (5).

The title compound was prepared in the same manner as described for 4, with the exception that compound 12 was used in place of compound 11, and the reaction time was 2 days. The title compound was obtained as a white solid (78%). m.p. 75–77° C.; $^1$H NMR (500 MHz, CDCl$_3$) δ 7.84–7.80 (m, 2H), 7.44–7.38 (m, 2H), 7.24–7.20 (m, 1H), 7.09–7.04 (m, 4H), 3.25–3.15 (m, 2H), 3.02–2.97 (m, 1H), 2.76 (t, J=4.3 Hz, 1H), 2.49 (dd, J=3.0 and 5.0 Hz, 1H), 2.19–2.10 (m, 1H), 1.86 (m, 1H); $^3$C NMR (125 MHz, CDCl$_3$) δ 162.93, 155.02, 130.58, 130.81, 125.47, 120.69, 117.91, 53.15, 50.32, 47.29, 26.23; IR(KBr disc) 3040 (s), 1580 (s), 1490 (s), 1320 (s), 1248 (s), 1148 cm$^{-1}$; m/z (EI) 304 (M$^+$, 80%), 233 (50), 217 (100); HRMS (EI) calcd. for C$_{16}$H$_{16}$O$_4$S 304.0769, found 304.0768.

(A.) 4-(4-Phenoxyphenylsulfanyl)-1-butene (12).

The title compound was prepared in the same manner as described for 11, with the exception that 4-bromo-1-butene was used in place of allyl bromide. Compound 12 was obtained as a colorless oil (88%). $^1$H NMR (400 MHz, CDCl$_3$) δ 7.37–7.32 (m, 4H), 7.14–7.10 (m, 1H), 7.04–7.00 (m, 2H), 6.96–6.88 (m, 2H), 5.90–5.80 (m, 1H), 5.12–5.02 (m, 2H), 2.98 (m, 2H), 2.41–2.34 (m, 2H); $^{13}$C NMR (100 MHz, CDCl$_3$) δ 157.18, 156.50, 136.65, 132.57, 130.05, 123.72, 119.55, 119.21, 116.47, 34.65, 33.71; IR(film) 3076 (w), 2923 (w), 1583 (s), 1485 (s), 1239 (s) cm$^{-1}$; m/z (EI) 256 (M$^+$, 100%), 215 ([M-allyl]$^+$, 90), 202 (15); HRMS (EI) calcd. for C$_{16}$H$_{16}$OS 256.0922 found 256.0922.

Example 3
3-(4-Phenoxyphenylsulfonyl)propyloxirane (6).

The title compound was prepared in the same manner as described for 4, with the exception that compound 13 was used in place of compound 11, and that the reaction time was 3 days. The title compound was obtained as a white solid (94%). $^1$H NMR (500 MHz, CDCl$_3$) δ7.86–7.80 (m, 2H), 7.44–7.39 (m, 2H), 7.25–7.22 (m, 1H), 7.10–7.04 (m, 4H), 3.21–3.08 (m, 2H), 2.90–2.86 (m, 1H), 2.74 (t, J=4.5 Hz, 1H), 2.45 (dd, J=2.5 and 4.5 Hz, 1H), 1.92 (quin, J=7.0 Hz, 2H), 1.85–1.78 (m, 1H), (m, 1H); $^{13}$C NMR (125 MHz, CDCl$_3$) δ 162.84, 155.08, 130.58, 130.48, 125.43, 120.70, 117.88, 56.28, 51.64, 46.86, 31.17, 20.12; IR(KBr disc) 3063 (w), 2923 (w), 1582 (s), 1488 (s), 1294 (s), 1246 (s), 1142 (s) cm$^{-1}$; m/z (EI) 318 (M$^+$, 40%), 290 (20), 217 (100%); HRMS (EI) calcd. for C$_{17}$H$_{18}$O$_4$S 318.0926, found 318.0924.

(A.) 5-(4-Phenoxyphenylsulfanyl)-1-pentene (13).

The title compound was prepared in the same manner as described for 11, with the exception that 5-bromo-1-pentene was used in place of allyl bromide. The title compound was obtained as a colorless oil (65%). $^1$H NMR (500 MHz, CDCl$_3$) δ 7.37–7.34 (m, 4H), 7.13–7.09 (m, 1H), 7.03–7.00 (m, 2H), 6.96–93 (m, 2H), 5.83–5.74 (m, 1H), 5.06–4.98 (m, 2H), 2.88 (t, J=7.0 Hz, 2H), 2.22–2.16 (m, 2H), 1.73 (q, J=7.0 Hz, 2H); $^{13}$C NMR (125 MHz, CDCl$_3$) δ 157.23, 156.36, 137.84, 132.30, 130.41, 130.03, 123.67, 119.55, 119.16, 115.62, 34.61, 32.86, 28.61; IR(film) 3075 (w), 2929 (m), 1583 (s), 1484 (s), 1236 (s) cm$^{-1}$; m/z (EI) 270 (M$^+$, 100%), 215 (70), 202 (60); HRMS (EI) calcd. for C$_{17}$H$_{18}$OS 270.1078, found 270.1076.

Example 4
(4-Phenoxyphenylsulfonyl)methylthiirane (1).

To a solution of compound 4 (710 mg, 2.5 mmol) in THF (5 mL), a solution of ammonium thiocyanate (559 mg, 7.4 mmol) in water (3 mL) was added. The reaction was stirred at room temperature for 16 hours, after which time it was poured into ethyl acetate (100 mL), and then washed with water (25 mL), followed by brine (25 mL). The organic phase was dried over magnesium sulfate and was concentrated to give a white oil. The crude material was purified by column chromatography (silica, 8:1 hexanes:ethyl acetate) to obtain compound 1 as a white solid (102 mg, 14%). m.p. 99–101° C.; $^1$H NMR (500 MHz, CDCl$_3$) δ 7.89–7.84 (m, 2H), 7.46–7.40 (m, 2H), 7.26–7.22 (m, 1H), 7.11–6.96 (m, 4H), 3.52 (dd, J=5.5 and 14.5 Hz, 1H), 3.17 (dd, J=7.5 and 14.5 Hz, 1H), 3.09–3.03 (m, 1H), 2.53 (dd, J=2.0 and 6.0 Hz, 1H) 2.16 (dd, J=2.0 and 5.0 Hz, 1H); $^{13}$C NMR (125 MHz, CDCl$_3$) δ 163.20, 155.02, 132.13, 130.95, 130.52, 125.52, 120.69, 117.97, 62.90, 26.31, 24.47; IR(KBr disc) 3030 (w), 1583 (s), 1486 (s), 1317 (s), 1246 (s), 1141 (s) cm$^{-1}$; m/z (EI) 306 (M$^+$, 2%), 242 ([M-SO$_2$]$^+$, 35); HRMS (EI) calcd. for C$_{15}$H$_{14}$O$_3$S$_2$ 306.0384, found 306.0382.

Example 5
2-(4-Phenoxyphenylsulfonyl)ethylthiirane (2).

The title compound was prepared in the same manner as described for 1, with the exception that compound 5 was used in place of compound 4. The crude material was purified by column chromatography (silica, 2:1 hexanes-:ethyl acetate) to give the title compound as a white solid (93%). m.p. 99–101° C.; $^1$H NMR (500 MHz, CDCl$_3$) 87.83 (d, J=8.0 Hz, 2H), 7.42 (t, J=8.0 Hz, 2H), 7.26–7.22 (m, 1H), 7.10–7.06 (m, 4H), 3.30–3–20 (m, 2H), 2.98–2.92 (m, 1H), 2.52 (dd, J=1 and 6 Hz, 1H), 2.48–2.39 (m, 1H), 2.18 (dd, J=1 and 5 Hz, 1H), 1.78–1.69 (m, 1H); $^{13}$C NMR (125 MHz, CDCl$_3$) δ 162.94, 155.03, 132.50, 130.55, 130.51, 125.48, 120.71, 117.92, 55.97, 33.62, 29.82, 26.05; IR(KBr disc) 3040 (w), 1583 (s), 1487 (s), 1256 (s), 1142 (s) cm$^{-1}$; m/z (EI) 320 (M$^+$, 50%), 288,(20), 234 (40), 217 (60), 170 (100); HRMS (EI) calcd. for C$_{16}$H$_{16}$O$_3$S$_2$ 320.0541, found 320.0540.

Example 6
3-(4-Phenoxyphenylsulfonyl)propylthiirane (3).

The title compound was prepared in the same manner as described for 1, with the exception that compound 6 was used in place of compound 4. The crude material was purified by column chromatography (silica, 2:1 hexanes-:ethyl acetate) to give the title compound as a white solid (85%). m.p. 75–76° C.; $^1$H NMR (500 MHz, CDCl$_3$) δ 7.85–7.82 (m, 2H), 7.44–7.40 (m, 2H), 7.26–7.22 (m, 1H), 7.10–7.06 (m, 4H), 3.20–3.09 (m, 2H), 2.84–2.79 (m, 1H), 2.50 (dd, J=1 and 6 Hz, 1H), 2.14 (dd, J=1 and 5.5 Hz, 1H), 2.12–2.06 (m, 1H), 1.97 (quin, J=8 Hz, 2H), 1.45–1.38 (m, 1H); $^{13}$C NMR (125 MHz, CDCl$_3$) δ 162.85, 155.08, 132.55, 130.60, 130.49, 125.43, 120.69, 117.91, 56.09, 35.13, 34.86, 25.72, 22.92; IR(KBr disc) 3000 (w), 1583 (s), 1480 (s), 1254 (s), 1143 (s) cm$^{-1}$; m/z (EI) 334 (M$^+$, 30%), 301 (10), 234 (100), 217 (70), 170 (70); HRMS (EI) calcd. for C$_{17}$H$_{18}$O$_3$S$_2$ 334.0697, found 334.06.

Example 7

TABLE 1

Kinetics parameters for inhibition of MMPs by compounds of the present invention

| | $k_{on}(M^{-1}s^{-1}) \times 10^{-4}$ | $k_{off}(s^{-1}) \times 10^3$ | $K_i(\mu M)$ |
|---|---|---|---|
| Compound 1 | | | |
| MMP-2 | 11 ± 1 | 1.5 ± 0.6a<br>1.8 ± 0.1 | 0.0139 ± 0.0004 |
| MMP-9 | 1.4 ± 0.3 | 9 ± 1$^a$<br>7.1 ± 0.5 | 0.6 ± 0.2 |
| MMP-3 | (1.8 ± 0.4) ± 10$^{-2}$ | 2.7 ± 0.9$^a$<br>5.5 ± 0.4 | 15 ± 6 |
| MMP-7 | | | 96 ± 41 |
| Compound 2 | | | |
| MMP-2 | | | 4.7 ± 0.7 |
| MMP-9 | | | 44 ± 5 |
| MMP-3 | | | NI$^b$ |
| MMP-7 | | | NI |
| MMP-1 | | | NI |
| Compound 3 | | | |
| MMP-2 | | | 4.3 ± 0.7 |
| MMP-9 | | | 181 ± 41 |
| MMP-3 | | | NI |
| MMP-7 | | | NI |
| MMP-1 | | | NI |
| Compound 4 | | | |
| MMP-2 | | | 25 ± 2 |
| MMP-9 | | | 186 ± 11 |
| MMP-3 | | | NI |
| MMP-7 | | | NI |
| MMP-1 | | | NI |
| TIMP-1$^c$ | | | |
| MMP-2 | 4.4 ± 0.1 | 1.3 ± 0.2 | 0.029 ± 0.005 |
| MMP-9 | 5.2 ± 0.1 | 1.2 ± 0.2 | 0.024 ± 0.004 |
| TIMP-2$^c$ | | | |
| MMP-2 | 3.3 ± 0.1 | 0.8 ± 0.1 | 0.023 ± 0.004 |
| MMP-9 | 2.2 ± 0.1 | 1.3 ± 0.2 | 0.058 ± 0.007 |
| Compound 5 | | | |
| MMP-2 | | | 5.1 ± 0.5 |
| MMP-9 | | | 102 ± 2 |
| MMP-3 | | | NI$^a$ |
| MMP-7 | | | NI |
| MMP-1 | | | NI |
| Compound 6 | | | |
| MMP-2 | | | 10.7 ± 0.6 |
| MMP-9 | | | 75 ± 6 |
| MMP-3 | | | NI$^b$ |
| MMP-7 | | | NI |
| MMP-1 | | | NI |

$^a$Determined by two different methods, hence the set of two numbers.
$^b$NI, for "not inhibiting", even at high concentrations of 130–330 μM.
$^c$Kinetic parameters for the high-affinity site for TIMPs were reported earlier in Olson, M. W.; Gervasi, D. C. ; Mobashery, S.; Fridman, R., J. Biol. Chem., 1997, 272, 29975–29983.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention. In addition, some references were obtained on the world wide web (www). These references are also incorporated by reference herein, as though individually incorporated by reference.

What is claimed is:

1. A compound of formula (I):

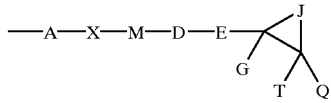

wherein
A—X—M is a hydrophobic group;
D is S, SO$_2$, or SO,
E is a direct bond, (C$_1$–C$_6$)alkyl, (C$_3$–C$_8$)cycloalkyl, (C$_2$–C$_6$)alkenyl, or (C$_2$–C$_6$)alkynyl, wherein any alkyl, cycloalkyl, alkenyl, or alkynyl of E is optionally substituted with one or more (C$_1$–C$_6$)alkyl, hydroxy, (C$_1$–C$_6$)alkoxy, cyano, nitro, halo, SR, NRR, or COOR, wherein each R is independently H or (C$_1$–C$_6$)alkyl;
J is S or O;
G, T, and Q are each independently H, (C$_1$–C$_6$)alkyl, or cyano;
or a pharmaceutically acceptable salt thereof.

2. The compound of claim 1 wherein A—X—M is a saturated or partially unsaturated hydrocarbon chain comprising one or more carbon atoms and optionally comprising one or more oxy (—O—), thio (—S—), sulfinyl (—SO—), sulfonyl (S(O)$_2$—), or NR$_f$ in the chain, wherein each R$_f$ is independently hydrogen or (C$_1$–C$_6$)alkyl;
wherein the saturated or partially unsaturated hydrocarbon chain is optionally substituted with one or more oxo (=O), hydroxy, cyano, halo, nitro, trifluoromethyl, trifluoromethoxy, (C$_1$–C$_6$)alkyl, (C$_1$–C$_6$)alkoxy, (C$_1$–C$_6$)alkoxy(C$_1$–C$_6$)alkyl, (C$_3$–C$_8$)cycloalkyl, aryl, heteroaryl, (C$_3$–C$_8$)cycloalkyl(C$_1$–C$_6$)alkyl, (aryl)(C$_1$–C$_8$)alkyl (heteroaryl)(C$_1$–C$_6$)alkyl, (C$_3$–C$_8$)cycloalkyl oxy, (aryl)oxy, (heteroaryl)oxy, (C$_3$–C$_8$)cycloalkyl, (aryl)oxy(aryl), (heteroaryl)oxy (heteroaryl), (C$_3$–C$_8$)cycloalkyl oxy (C$_1$–C$_6$)alkyl, (aryl)oxy (C$_1$–C$_6$)alkyl, or (heteroaryl)oxy (C$_1$–C$_6$) alkyl; and
wherein any aryl, (C$_3$–C$_8$)cycloalkyl, or heteroaryl is optionally substituted with one or more oxo (=O), hydroxy, cyano, halo, nitro, trifluoromethyl, trifluoromethoxy, (C$_1$–C$_6$)alkyl, (C$_1$–C$_6$)alkoxy, (C$_1$–C$_6$)alkoxy(C$_1$–C$_6$)alkyl, (C$_3$–C$_8$)cycloalkyl, aryl, heteroaryl, (C$_3$–C$_8$)cycloalkyl(C$_1$–C$_6$)alkyl, (aryl) (C$_1$–C$_8$)alkyl, (heteroaryl)(C$_1$–C$_6$)alkyl, (C$_3$–C$_8$) cycloalkyl oxy, (aryl)oxy, (heteroaryl)oxy, (C$_3$–C$_8$) cycloalkyl, (aryl)oxy(aryl), (heteroaryl)oxy (heteroaryl), (C$_3$–C$_8$)cycloalkyl oxy (C$_1$–C$_6$)alkyl, (aryl)oxy (C$_1$–C$_6$)alkyl, or (heteroaryl)oxy (C$_1$–C$_6$) alkyl.

3. The compound of claim 1 wherein A and M are each independently phenyl or monocyclic heteroaryl, wherein any phenyl or monocyclic heteroaryl is optionally substituted with one or more hydroxy, (C$_1$–C$_6$)alkyl, (C$_1$–C$_6$) alkanoyl, (C$_1$–C$_6$)alkanoyloxy, (C$_1$–C$_6$)alkoxy, cyano, nitro, halo, trifluoromethyl, trifluoromethoxy, SR, NRR, or COOR; and
X is O, S, SO, SO$_2$, C(=O)NR, C(=O)O, NRC(=O), OC(=O), NR, a direct bond, or (C$_1$–C$_6$)alkyl optionally substituted with one or more hydroxy, $(C_1-C_6)$ alkoxy, cyano, nitro, halo, SR, NRR, or COOR.

4. The compound of claim 1 wherein A—X—M is bicyclic aryl, bicyclic heteroaryl, or bicyclic alkyl; wherein any aryl, heteroaryl or alkyl is optionally substituted with one or more hydroxy, $(C_1-C_6)$alkyl, $(C_1-C_6)$alkanoyl, $(C_1-C_6)$alkanoyloxy, $(C_1-C_6)$alkoxy, cyano, nitro, halo, trifluoromethyl, trifluoromethoxy, SR, NRR, or COOR; wherein each R is independently H, $(C_1-C_6)$alkyl, phenyl, benzyl, or phenethyl.

5. The compound of claim 1 wherein A—X—M is bicyclic aryl, bicyclic heteroaryl, or bicyclic alkyl.

6. The compound of claim 1 wherein A—X—M is:

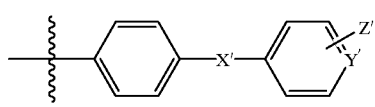

wherein

X' is O, CH$_2$, or a direct bond;

Y' is N or CH$_2$; and

Z' is halo, OCH$_3$, or hydroxy.

7. The compound of claim 1 wherein A—X—M is:

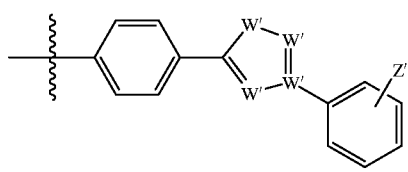

wherein each W' is independently N or CH; and

Z' is halo, OCH$_3$, or hydroxy.

8. The compound of claim 1 wherein A—X—M is:

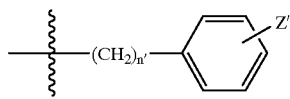

wherein n' is about 1 to about 4; and

Z' is halo, OCH$_3$, or hydroxy.

9. The compound of claim 1 wherein A—X—M is:

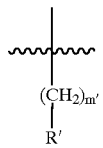

wherein

R' is O, CH$_2$, or S; and m' is about 2 to about 7.

10. The compound of claim 1 wherein A—X—M is:

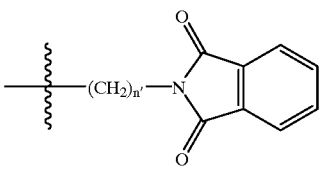

wherein n' is about 1 to about 4.

11. The compound of claim 1 wherein A—X—M is:

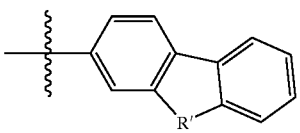

wherein

R' is O, CH$_2$, or S.

12. The compound of claim 1 wherein A—X—M is naphthyl.

13. The compound of claim 1 wherein A is phenyl.

14. The compound of claim 1 wherein M is phenyl.

15. The compound of claim 1 wherein X is O.

16. The compound of claim 1 wherein E is $(C_1-C_6)$alkyl.

17. The compound of claim 1 wherein E is methyl.

18. The compound of claim 1 wherein J is S.

19. The compound of claim 1 wherein G is hydrogen.

20. The compound of claim 1 wherein T is hydrogen.

21. The compound of claim 1 wherein Q is hydrogen.

22. The compound of claim 1 wherein A is phenyl, M is phenyl, X is O, D is SO$_2$, E is methyl, J is S, G is hydrogen, T is hydrogen, and Q is hydrogen.

23. A pharmaceutical composition comprising a compound of claim 1; and a pharmaceutically acceptable carrier.

24. A radiolabeled compound comprising a compound of formula (I) as described in claim 1, and a radionuclide.

25. The compound of claim 24 wherein the radionuclide is a non-metallic radionuclide.

26. The compound of claim 25 wherein the non-metallic radionuclide is Fluortne-19, Carbon-11, Fluorine-18, Iodine-123, or Bromine-76.

27. The compound of 24 wherein the compound comprises a chelating group comprising a detectable radionuclide.

28. The compound of claim 27 wherein the detectable radionuclide is a metallic radionuclide.

29. The compound of claim 28 wherein the metallic radionuclide is Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gold-195, Gold-199, Hafnium-175, Hafnium-175–181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, or Zirconium-95.

30. A pharmaceutical composition comprising a compound of claim 24, and a pharmaceutically acceptable carrier.

\* \* \* \* \*

UNITED STATES PATENT AND TRADEMARK OFFICE
CERTIFICATE OF CORRECTION

PATENT NO.    : 6,703,415 B2
DATED         : March 9, 2004
INVENTOR(S)   : Mobashery et al.

It is certified that error appears in the above-identified patent and that said Letters Patent is hereby corrected as shown below:

Title page, Item [54] and Column 1, line 2,
Title, delete "METALLAPROTEINASES" and insert
-- METALLAPROTEINASES --, therefor.

Title page,
Item [22], Filed Date, delete "May 3, 2001" and insert -- May 30, 2001 --, therefor.
Item [56], References Cited, OTHER PUBLICATIONS,
"Brew et al.," reference, delete "Biochim." and insert -- Biochem. --, therefor.
"Greenwal, R. A. et al.," reference, delete "Metalloproteinase" and insert
-- Metalloproteinases --, therefor.
"Nelson, A. R. et al.," reference, delete "Biolegic" and insert -- Biologic --, therefor.
"Salo et al.," reference, after "258," insert -- (1983), --.

Column 1,
Line 20, after "FASEB J" insert -- . --.
Lines 21 and 40, after "J" insert -- . --.
Line 32, delete "Biochim." and insert -- Biochem. --, therefor.
Line 48, delete "BioL" and insert -- Biol. --, therefor.
Line 61, after "Y" insert -- . --.
Line 66, delete "inplantation" and insert -- implantation --, therefor.

Column 3,
Line 27, delete "La.," and insert -- LA, --, therefor.
Line 36, delete "Suth" and insert -- Such --, therefor.
Line 45, delete "-" before "A".

Column 4,
Line 6, delete "(J)" and insert -- (I) --, therefor.
Line 19, after "prevention" insert -- of --.
Lines 50 and 56, after "compound" insert -- of --.

UNITED STATES PATENT AND TRADEMARK OFFICE
CERTIFICATE OF CORRECTION

PATENT NO. : 6,703,415 B2
DATED : March 9, 2004
INVENTOR(S) : Mobashery et al.

It is certified that error appears in the above-identified patent and that said Letters Patent is hereby corrected as shown below:

Column 5,
Line 36, after "O" insert -- , --.
Line 63, delete ""fertilization"" and insert -- "fertilization" --, therefor.

Column 6,
Line 16, delete ""fertilization"" and insert -- "fertilization" --, therefor.
Line 60, after "Chemistry" insert -- , --.

Column 7,
Lines 7 and 17, after "NY," delete "N.Y.".
Line 14, delete "nucleoplic" and insert -- nucleophilic --, therefor.
Line 59, delete "Rf" and insert -- $R_f$ --, therefor.

Column 8,
Line 35, after "is O" insert -- , --.

Column 10,
Line 9, delete "Kames" and insert -- Karnes --, therefor.
Line 31, delete "0" and insert -- O --, therefor.

Column 13,
Line 18, after "157" insert -- , --.

Column 14,
Line 50, delete "http//" and insert -- http:// --, therefor.

Column 15,
Line 3, delete "standard_mechanism list.html" and insert
-- standard_mechanism_list.html --, therefor.
Liens 52 - 53, delete "cis-diamminedichloroplatimun" and insert
-- cis-diamminedichloroplatinum --, therefor.

UNITED STATES PATENT AND TRADEMARK OFFICE
CERTIFICATE OF CORRECTION

PATENT NO. : 6,703,415 B2
DATED : March 9, 2004
INVENTOR(S) : Mobashery et al.

It is certified that error appears in the above-identified patent and that said Letters Patent is hereby corrected as shown below:

Column 18,
Line 56, "Ky." and insert -- KY --, therefor.

Column 19,
Line 23, delete "Ky." and insert -- KY --, therefor.

Column 20,
Line 34, delete "confornational" and insert -- conformational --, therefor.

Column 22,
Line 34, delete "$C_{15}H_5NO_2S$" and insert -- $C_{15}H_{15}NO_2S$ --, therefor.
Line 46, after "1581 (s)" insert -- , --.
Line 61, delete "1H" and insert -- $^1H$ --, therefor.

Column 23,
Line 11, after "chromatography" delete ",".
Line 18, delete "(M+, 100%)" and insert -- ($M^+$, 100%) --, therefor.
Line 32, delete "$^3C$" and insert -- $^{13}C$ --, therefor.

Column 24,
Line 45, delete "87.83" and insert -- $\delta$ 7.83 --, therefor.
Line 47, delete "3.30-3-20" and insert -- 3.30-3.20 --, therefor.

Column 25,
Line 18, delete "1.5± 0.6a" and insert -- 1.5± $0.6^a$ --, therefor.
Line 22, delete "(1.8 ± 0.4) ± $10^{-2}$" and insert -- (1.8 ± 0.4) × $10^{-2}$ --, therefor.

Column 26,
Line 10, Formula I, delete "–" before "A".

Column 28,
Line 47, delete "Fluortne-19" and insert -- Fluorine-19 --, therefor.
Line 62, after "157" insert -- , --.

UNITED STATES PATENT AND TRADEMARK OFFICE
CERTIFICATE OF CORRECTION

PATENT NO. : 6,703,415 B2
DATED : March 9, 2004
INVENTOR(S) : Mobashery et al.

It is certified that error appears in the above-identified patent and that said Letters Patent is hereby corrected as shown below:

Column 30,
Line 5, delete "," and insert -- ; --, therefor.

Signed and Sealed this

Thirty-first Day of August, 2004

JON W. DUDAS
*Director of the United States Patent and Trademark Office*